(12) United States Patent
Braun

(10) Patent No.: US 9,619,767 B2
(45) Date of Patent: *Apr. 11, 2017

(54) METHOD AND APPARATUS FOR TRACKING AND MAINTAINING EMERGENCY EQUIPMENT

(71) Applicant: Emergency University, Inc., Emerald Hills, CA (US)

(72) Inventor: Odelia Braun, Redwood City, CA (US)

(73) Assignee: EMERGENCY UNIVERSITY, INC., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/516,178

(22) Filed: Oct. 16, 2014

(65) Prior Publication Data
US 2015/0112704 A1     Apr. 23, 2015

Related U.S. Application Data

(63) Continuation-in-part of application No. 14/269,030, filed on May 2, 2014, now Pat. No. 9,324,120.
(Continued)

(51) Int. Cl.
*G06Q 50/26*        (2012.01)
*G06Q 10/06*        (2012.01)
(Continued)

(52) U.S. Cl.
CPC ....... *G06Q 10/0631* (2013.01); *G06F 19/327* (2013.01); *G06Q 10/00* (2013.01);
(Continued)

(58) Field of Classification Search
USPC .......................................................... 705/325
See application file for complete search history.

(56) References Cited

U.S. PATENT DOCUMENTS

| 5,960,337 | A  | 9/1999 | Brewster et al. |
| 7,048,185 | B2 | 5/2006 | Hart |

(Continued)

FOREIGN PATENT DOCUMENTS

| WO | 0225319 A2 | 3/2002 |
| WO | WO-2013142900 | 10/2013 |

*Primary Examiner* — Kathleen Palavecino
*Assistant Examiner* — Andrew Whitaker
(74) *Attorney, Agent, or Firm* — Perkins Coie LLP

(57) ABSTRACT

Embodiments of the invention provide a uniquely accountable mechanism to provide emergency responders with accurate and verifiable data regarding the location and operational readiness of emergency equipment immediately upon notification of an emergency. The invention tracks, records, and establishes workflows to maintain emergency medical equipment, such as automated external defibrillators (AEDs), by non-technical, non-healthcare providers for use by emergency responders in pre-hospital, pre-EMS medical emergencies. The unique and verifiable data obtained from this process is used as part of an emergency notification system that provides emergency responders, such as sudden cardiac arrest (SCA) responders, in an organizational setting, with immediate and accurate information identifying the nearest operationally ready medical device at the time of the emergency, which information has heretofore never been available to emergency responders such as SCA responders.

25 Claims, 15 Drawing Sheets

Related U.S. Application Data

(60) Provisional application No. 61/892,836, filed on Oct. 18, 2013.

(51) Int. Cl.

| | | |
|---|---|---|
| *G06Q 50/22* | (2012.01) | |
| *G06Q 10/00* | (2012.01) | |
| *G06Q 10/10* | (2012.01) | |
| *G06Q 10/08* | (2012.01) | |
| *G06F 19/00* | (2011.01) | |

(52) U.S. Cl.
CPC .......... *G06Q 10/087* (2013.01); *G06Q 10/10* (2013.01); *G06Q 10/20* (2013.01); *G06Q 50/22* (2013.01); *G06Q 50/265* (2013.01)

(56) References Cited

U.S. PATENT DOCUMENTS

| | | |
|---|---|---|
| 7,091,852 B2 | 8/2006 | Mason et al. |
| 7,171,217 B2 | 1/2007 | Beuck |
| 7,177,623 B2 | 2/2007 | Baldwin |
| 7,289,029 B2 | 10/2007 | Medema et al. |
| 7,607,014 B2 | 10/2009 | Larson et al. |
| 7,793,850 B1 | 9/2010 | Ho et al. |
| 7,922,073 B2 | 4/2011 | de la Huerga |
| 8,095,403 B2 | 1/2012 | Price |
| 8,185,623 B2 | 5/2012 | Lewis et al. |
| 8,300,922 B1 | 10/2012 | Garvey, III |
| 8,314,683 B2 | 11/2012 | Pfeffer |
| 8,350,693 B2 | 1/2013 | McSheffrey et al. |
| 8,401,514 B2 | 3/2013 | Ebdon et al. |
| 8,526,910 B2 | 9/2013 | Messerly |
| 2002/0026266 A1* | 2/2002 | Montague ............. B60R 25/102 701/1 |
| 2003/0069648 A1* | 4/2003 | Douglas ................. G06Q 10/20 700/2 |
| 2005/0190053 A1 | 9/2005 | Dione |
| 2007/0174438 A9 | 7/2007 | Johnson et al. |
| 2009/0284348 A1 | 11/2009 | Pfeffer |
| 2011/0117878 A1 | 5/2011 | Barash et al. |
| 2011/0130636 A1 | 6/2011 | Daniel et al. |
| 2011/0151829 A1 | 6/2011 | Velusamy et al. |
| 2012/0218102 A1* | 8/2012 | Bivens ................. G08B 25/003 340/539.13 |
| 2012/0232355 A1 | 9/2012 | Freeman |
| 2012/0271370 A1 | 10/2012 | Hochhalter et al. |
| 2013/0012151 A1 | 1/2013 | Hankins |
| 2013/0040600 A1 | 2/2013 | Reitnour et al. |
| 2013/0053063 A1* | 2/2013 | McSheffrey ........... G08B 7/066 455/456.1 |
| 2013/0252574 A1* | 9/2013 | Single ..................... H04W 4/22 455/404.2 |
| 2014/0002241 A1* | 1/2014 | Elghazzawi ........ H04W 76/007 340/8.1 |

\* cited by examiner

FIG. 11

AED Check

E_y ALERT!

5. There are 2 or more green battery lights lit (lift the lid and wait 10 seconds before reading battery lights).

☐ I have completed the checklist and this AED is in working order.

☐ LabelBattery needs replacing (less than 2 lights for #5 above).

☐ Not all conditions are met, I need assistance. (Describe the problem below and we will contact you, or call us at 1-866-AED-HELP)

Submit

FIG. 10

AED Check

E_y ALERT!

Cardiac Science Powerheart G3

Location: Bldg 1, first floor kitchen

1. The Rescue Ready light is green and there are no alarms or beeping sounds. (Show image)

2. AED clean and undamaged.

3. The electrode pads are available and sealed.

4. The emergency response/ready kit is intact (gloves, pocket mask, etc.)

5. There are 2 or more green battery lights lit (lift the lid and wait 10 seconds before reading battery lights).

☐ I have completed the checklist and this AED is in working order

METHOD AND APPARATUS FOR TRACKING AND MAINTAINING EMERGENCY EQUIPMENT

CROSS REFERENCE TO RELATED APPLICATIONS

This application is a continuation-in-part of U.S. patent application Ser. No. 14/269,030, filed May 2, 2014, and claims priority to U.S. provisional patent application Ser. No. 61/892,836, filed Oct. 18, 2013, each of which application is incorporated herein in its entirety by this reference thereto.

FIELD

The invention relates to tracking the location and operational readiness of emergency equipment. More particularly, the invention relates to providing an emergency responder with the accurate location of the nearest operationally ready emergency equipment to retrieve and use during an emergency within the operationally/clinically appropriate period of time.

BACKGROUND

Out-of-hospital, sudden cardiac arrests (SCA) claim the life of approximately 375,000 victims each year in the U.S. SCAs claim more lives than Alzheimer's, assault with firearms, breast cancer, colorectal cancer, HIV, diabetes, house fires, motor vehicle accidents, prostate cancer, suicides, and industrial accidents combined. Sudden cardiac arrest is most often caused by an abrupt deterioration of the heart's normal rhythm. This electrical rhythm, normal sinus rhythm, causes the heart to contract regularly and pump blood to the brain and throughout the body. In sudden cardiac arrest, the normal sinus rhythm abruptly deteriorates into a chaotic electrical rhythm, called ventricular fibrillation that fails to contract the heart. As a result, blood is not pumped out from the heart. The result is immediate unconsciousness and collapse, which, if untreated, progresses rapidly to death.

Since the 1970's, defibrillation has been the standard of care for cardiac arrests in medical settings, such as the hospital intensive care unit, the emergency room, or the ambulance. Defibrillation is the delivery of a therapeutic dose of electrical energy to the heart with a medical device called a defibrillator. In these medical settings, a manual defibrillator is used. The manual defibrillator requires a healthcare professional, usually a physician, to analyze the patient's heart rhythm on a cardiac monitor. When ventricular fibrillation is detected, the healthcare professional administers a shock to the heart with the defibrillator. The defibrillator's shock quiets the heart's chaotic rhythm and allows the heart's normal rhythm to take over. In this way, the defibrillator converts the heart's abnormal rhythm, ventricular fibrillation, back into the heart's normal rhythm, However, the majority of SCAs do not occur in medical settings where healthcare professionals and proper equipment are readily available. Unfortunately, the majority of sudden cardiac arrests occur in the community where people, live, work, and play. The cardiac arrest victim is usually located far away from healthcare professionals, and the life-saving medical equipment.

Prior to the late 1980's, nearly all patients who suffered a cardiac arrest out of the hospital died. The addition of the defibrillator for use by paramedics on ambulances improved survival, but the time required for paramedics to arrive to the scene of a cardiac emergency was still too long. Multiple research studies performed on out of hospital cardiac arrest, determined that "time to defibrillation" is the most significant determinant of whether the individual can survive the cardiac arrest. Studies have concluded that a defibrillatory shock must be applied to the heart within four minutes of collapse. Yet, most EMS response times are far in excess of four minutes. EMS response times are typically between 8 to 12 minutes.

To improve survival, the medical community embraced a new technology, the automated external defibrillator (AED), in the late 1980's. The AED is a computerized device that includes a software algorithm that was developed to read the victim's cardiac rhythm, and then advise the rescuer whether to press the shock button to apply a defibrillatory shock. In contrast to AEDs, manual defibrillators require that the healthcare provider using the medical device be familiar with cardiac rhythms, and be able to read the cardiac rhythm on a cardiac monitor which is attached to the patient's chest. The medical professional then determines whether or not a shock is indicated. The manual defibrillator plays the roll of delivering the shock, but does not diagnose the rhythm, nor determine whether a shock is indicated.

However, an AED assumes both that the individual using the device does not know how to read cardiac rhythms, and that the user would not be able to determine whether or not a shock is indicated. The AED itself includes an algorithm that analyzes the heart rhythm and determines whether or not a shock would be beneficial. Because the AED does not require any medical knowledge other than how to turn on the AED and follow the voice prompts, it can be used by non-healthcare providers, and can be located in the community where people live, work, and play, i.e. the locations where the majority of out-of-hospital sudden cardiac arrests occur. AEDs have been successfully used in the community by non-healthcare providers since 1988 in the U.S.

AEDs have been conclusively determined to read cardiac rhythms accurately, and properly advise whether a shock should be delivered. Their use by non-healthcare professionals has been proven to be safe. AED presence and use has expanded from the ambulance to the fire department to police departments, and in the last ten years to workplace settings, thus providing non-healthcare professionals, i.e. the lay public, the opportunity to provide the life-saving shock. Multiple reports in the medical literature have demonstrated that when an AED is applied prior to the arrival of emergency medical services (EMS), the chances of survival increase from approximately 8% to over 30%.

In 1993, the inventor recommended that organizations, such as corporate entities, should develop internal emergency response programs because of the time requirement to deliver a shock. These programs would include medical oversight, an emergency response plan, training and practice for members of the workforce to provide cardiopulmonary resuscitation (CPR) and operate an AED in their workplace, and proper maintenance of the AEDs installed at their facility. AED programs are implemented so that trained responders in an organization can provide CPR and the benefit of an AED to co-workers and visitors of the organization prior to the arrival of EMS. An important part of the program was to develop a system that would ensure that the AEDs would work properly when these medical devices were needed.

In the early 2000's, organizations began adopting the strategy of providing an onsite emergency response that included trained responders and AEDs. Some of the earliest adopters of AED Programs included airlines, such as American Airlines and United Airlines. The Federal Aviation Administration (FAA) mandated AED programs for all airlines that land in the United States.

As of 2013, more than two million AEDs have been sold, over one million of these to private sector organizations.

AEDs are composed of four parts:

1) The defibrillator unit, a computerized device that is capable of reading the cardiac rhythm, and advising whether or not a shock is indicated;

2) Batteries to power the device and the capacitor that delivers the shock;

3) Pads, that are to be placed on the patient's chest to read the cardiac rhythm, and deliver the shock; and 4) Connectors that connect that pads on the patient's chest to the defibrillator.

Currently, six major original equipment manufacturers (OEMs) manufacture and distribute eleven models of AEDs in the US. The major OEMs in the U.S. are Philips, Physio-Control, ZOLL Medical, HeartSine, Defibtech, and Cardiac Science.

An essential element of an AED program is establishing a system for proper maintenance of the AED unit itself. For example, AED pads expire between 2% and four years from the date of production, depending on the manufacturer's make and model, and require replacement. Similarly, AEDs use several types of batteries, including lithium batteries, and standard AA batteries, which expire between four and seven years from the time they are placed into service, and must be replaced. In addition, approximately 10-15% of AEDs have manufacturing errors that can occur on an individual device basis, or a design flaw on a make and model basis. These manufacturing and design errors typically require that the machine be repaired or replaced all together. Therefore, regular surveillance is required to ensure that the AED is properly functioning when it is needed in an emergency, such as a sudden cardiac arrest.

AED units perform automated daily self checks. During their daily self check, an AED unit tests itself to ensure that all of its parts meet minimum operational specifications. When an AED does not meet these minimum requirements, depending on the manufacturer's make and model, it beeps, turns off its ready light, and/or changes its status from a "✓" to an "x" to indicate a problem exists. Manufacturer recommendations for regular AED maintenance vary, but most, at the minimum require that an AED must be visually inspected once a month by an individual given responsibility for maintaining the proper functioning of the AED, usually called an AED coordinator, to determine if the AED is properly functioning.

This inspection process requires that the AED coordinator visually inspects the AED to ensure that the ready light is still blinking and that it is the correct color, and to ensure that the AED is not beeping or otherwise emitting a sound that indicates a problem exists. The AED coordinator must also ensure that pads and batteries are not expired and are still present, and that the AED unit has not been otherwise damaged or misplaced.

AED Device Failures

The U.S. Food and Drug Administration (FDA) regulates medical devices in the United States and collects post-approval data on device malfunctions. Patients, healthcare facilities, healthcare providers, or device manufacturers can report adverse events. FDA adverse event reporting is required by law if the device failure involves a patient fatality. Although the reporting is mandatory, it is likely that many non-healthcare professionals are unaware of this reporting requirement. In 2011, medical researchers performed a review of AED device failures reported to the FDA. They published their results in the Annals of Emergency Medicine. They reported that between 1993 and 2008, 40,787 AED adverse events were reported to the FDA. A fatality occurred in 1,284 of these AED adverse events. Researchers sought to determine the cause of the AED failure in these fatal events.

For cases, in which the researchers reasonably believed that they could draw a conclusion as to cause, they attributed approximately 50% of AED failures to battery or power problems, and 45% of AED failures to pads/connectors. A significant majority of these AED problems could have been detected by a reliable AED maintenance program following the manufacturer's recommended guidelines. When an AED Program is implemented at a new facility, a workforce volunteer is recruited to become the AED coordinator for that facility. One of this individual's ongoing responsibilities is to perform the monthly maintenance inspection of the AEDs in their facility. The AED coordinator can be in charge of inspecting between one and 30 AEDs, depending on the size of the facility, and the resources invested in the organization's AED Program.

Failure of Current AED Maintenance Systems

A systematic and sustainable AED maintenance program with strict accountability is lacking in the marketplace. The majority of AED maintenance programs in the industry use as their sole mechanism, an automated email notification system that sends reminder emails to perform monthly maintenance to the facility's designated AED coordinator.

AED program management providers typically collect the contact information for the AED coordinator, including their email address, and store this information in a database. Once the AEDs have been placed into service, the AED coordinator is sent an email notification on a monthly basis to perform the required AED maintenance.

AED programs based on automated email notification systems have failed for many reasons, including:

1) Technical failures, where emails fail to be received by the intended responsible party;

2) Personnel failures, where the responsible party fails to perform maintenance;

3) Lack of accountability, where there is a failure of the program vendor and/or manager to follow-up on the lack of performance by the responsible party; and 4) Lack of accountability, where there are inadequate mechanisms to determine if physical inspection of the device was actually performed.

Technical Failures

A variety of common technical issues cause AED program notification systems to fail. Notification emails may not reach the intended recipient because of technical errors, such as inaccurate data acquisition or data entry, such as simple spelling errors, or data input errors. Notification emails also fail because the recipient's email server inadvertently blocks it, especially with common email carriers such as Hotmail, AOL, Yahoo, or Google. The recipient's email server may also misdirect the email to the Junk or Spam folder. Any of these technical errors result in lack of notification of the responsible party.

Personnel Failures

Approximately 25% of AED coordinators discontinue providing maintenance due to relocation to another facility, reassignment to other job responsibilities, illness, retirement, or leaving the company. Often, another AED coordinator is not designated because the organization does not realize that maintenance is no longer being performed.

Reassignment of this responsibility often is overlooked because the AED coordinators are volunteers, and performing maintenance is not part of their official job description. Other AED coordinators simply believe they are too busy or are not motivated to complete their AED maintenance responsibilities. They often do not notify the organization that they are no longer willing to perform their AED maintenance responsibilities. The result is that any AED device for which the party is responsible is no longer properly monitored and maintained. This significantly increases the risk that when the AED is required for a sudden cardiac arrest, it does not function properly, and a life is not saved.

Lack of Accountability

Lack of Follow-Up when Timely Maintenance is not Performed

Email notification systems are automated database-driven systems that routinely lack back-up mechanisms, such as people, to contact AED coordinators who are not performing the required timely maintenance. Typically, an AED coordinator's failure to perform the required in-person maintenance occurs because:

1) The AED coordinator did not receive emails notifying him of the need to perform maintenance;

2) The AED coordinator is no longer working in the facility; and

3) The AED coordinator no longer wishes to perform the AED maintenance responsibilities.

The vast majority of AED program vendors who use automated email notification systems provide no personal follow up when maintenance is not properly completed.

Lack of Confirmation that Required Inspection was Actually Performed

Lack of accountability also exists because of inadequate mechanisms to confirm that the required timely maintenance was actually performed as reported. Email notification systems require only that the recipient responds to the email notification or enters a response into the AED management database indicating that a physical inspection has been performed. Because AED coordinators are volunteers, and the AED program is seldom part of the organization's core business, nor the AED coordinator's job description, and the AED coordinator may simply electronically respond to the automated notification email rather than perform the required physical inspection. Simply checking the required box electronically to confirm that the email has been received provides no assurance that the AED is properly maintained.

In the inventor's experience, based on 24 years of managing AED programs, when an organization's AED program is audited to determine:

1) If the organization knows the location of their AEDs;

2) The name of the AED coordinator responsible for each AED;

3) If proper maintenance has been performed resulting in a functioning AED; and

4) If pads and batteries are expired, the result is that a minimum of 25-35% of AEDs are not in compliance. Of the non-compliant AEDs, 20% of the devices do not have an active AED coordinator assigned, or their location is not known. An additional 10-15% of the machines have an assigned AED coordinator who is unwilling to perform the physical inspection.

These findings and the lack of accountability for maintaining functioning AEDs are major contributors to the significant number of AED failures reported to the FDA.

SUMMARY

Embodiments of the invention provide a uniquely accountable mechanism to provide emergency responders with accurate and verifiable data regarding the location and operational readiness of emergency equipment immediately upon notification of an emergency. The invention tracks, records, and establishes workflows to maintain emergency medical equipment, such as automated external defibrillators (AEDs), by non-technical, non-healthcare providers for use by emergency responders in pre-hospital, pre-EMS medical emergencies. The unique and verifiable data obtained from this process is used as part of an emergency notification system that provides emergency responders, such as sudden cardiac arrest (SCA) responders, in an organizational setting, with immediate and accurate information identifying the nearest operationally ready medical device at the time of the emergency, which information has heretofore never been available to emergency responders such as SCA responders.

DRAWINGS

FIGS. 10 and 11 are screen shots showing an AED checklist according to the invention;

DESCRIPTION

Figure 1:
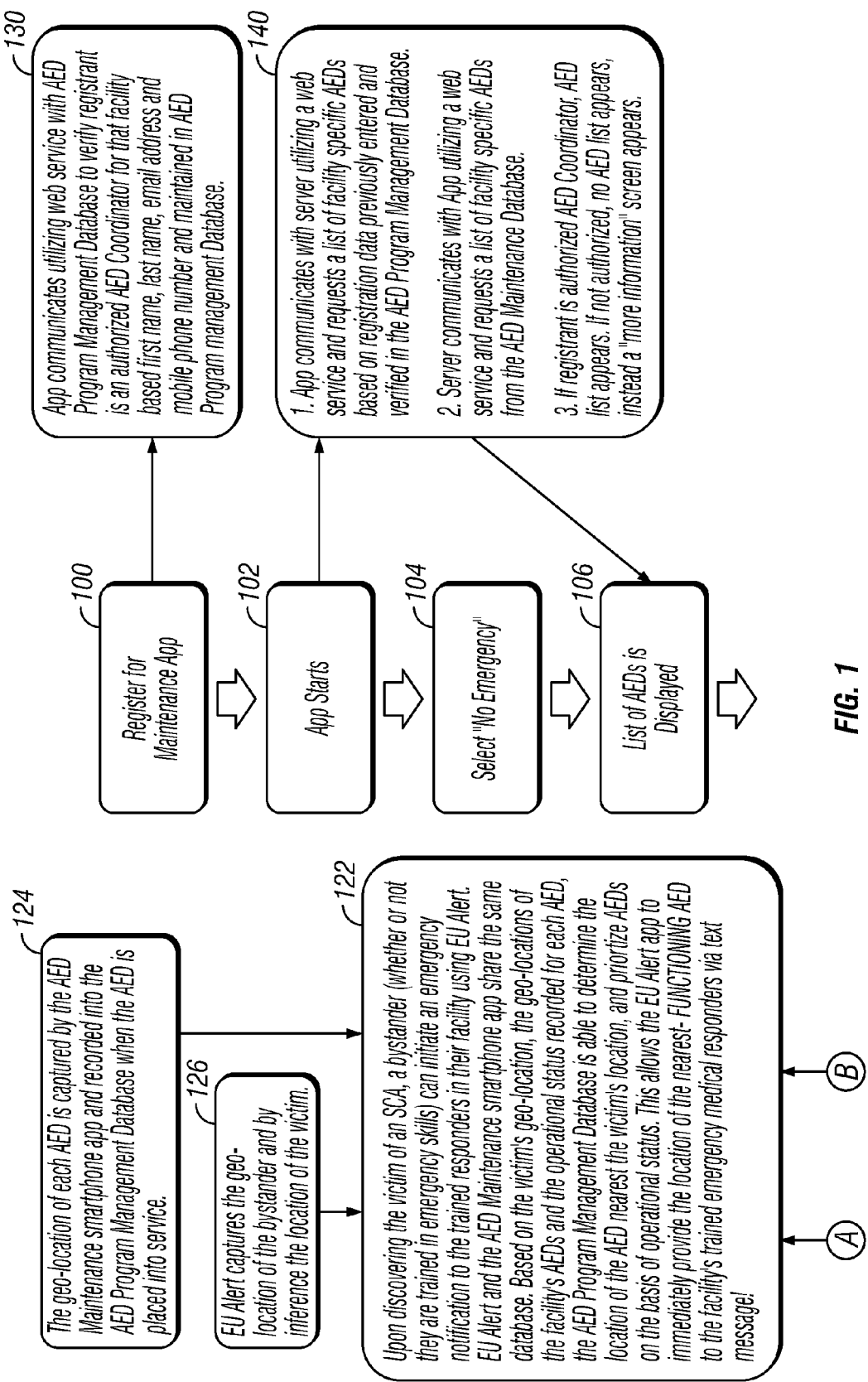
FIG. 1 is a flow diagram showing a method for tracking and maintaining emergency equipment according to the invention.
Figure 1:
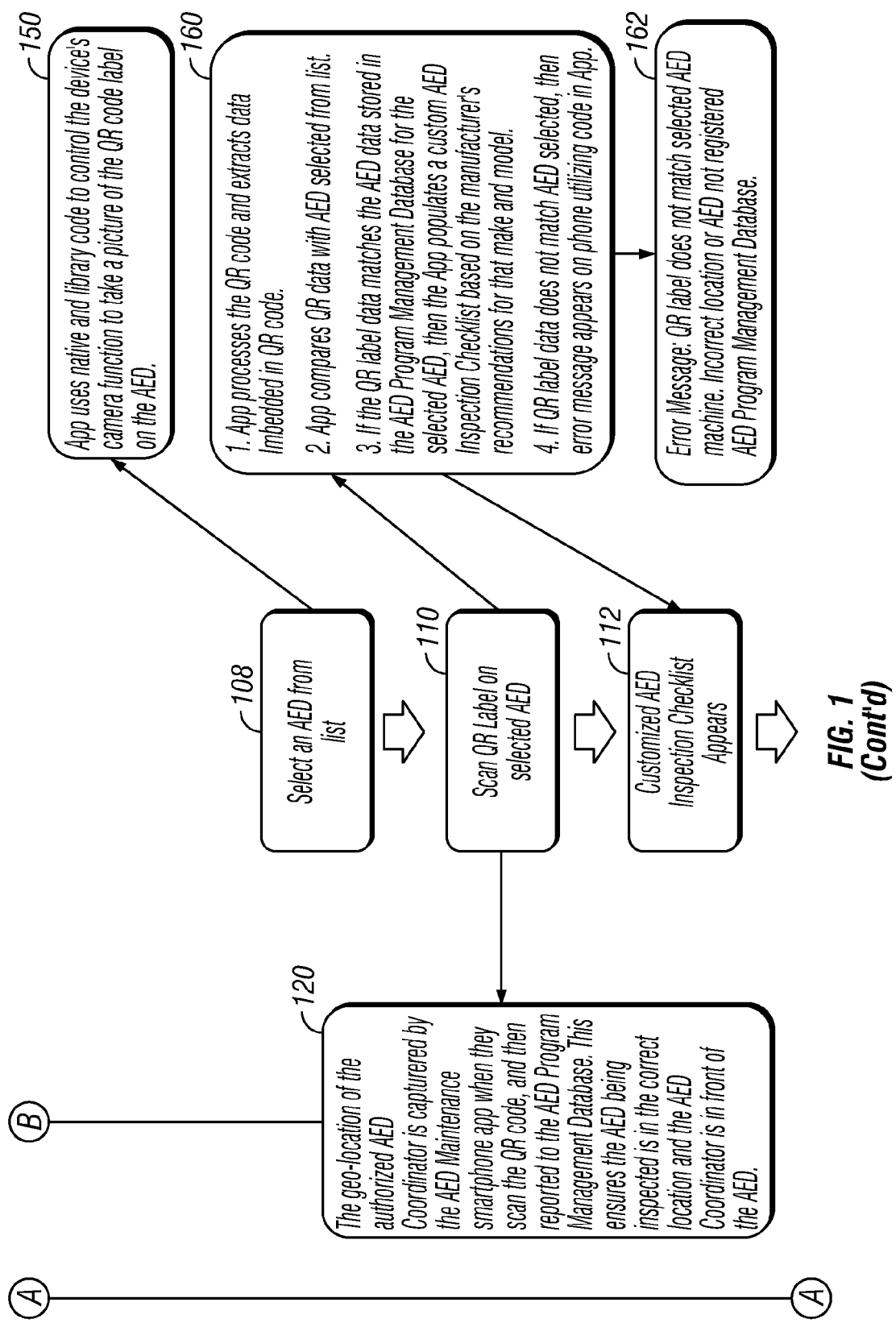
Figure 1:
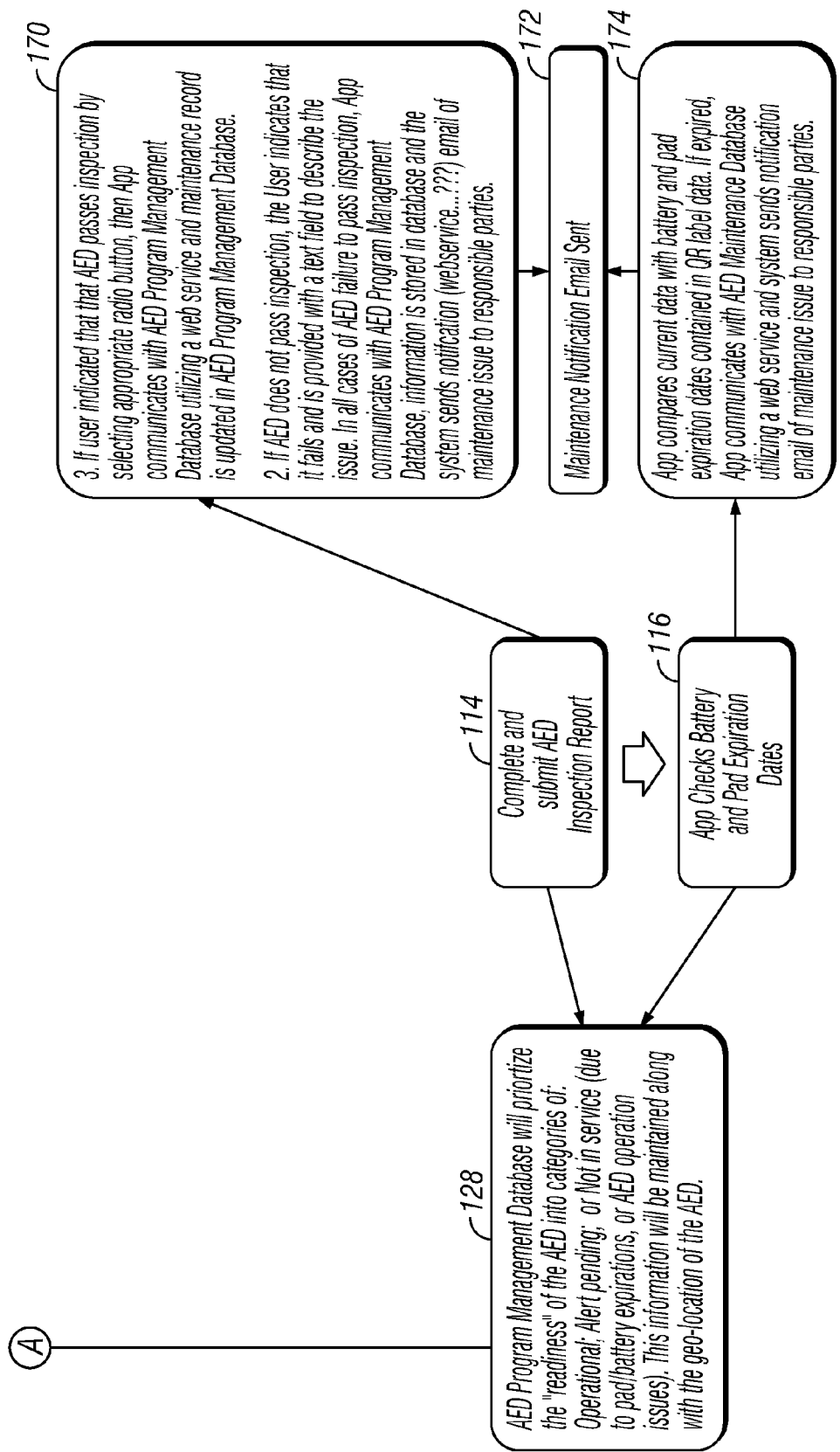

Embodiments of the invention provide a uniquely accountable mechanism to provide emergency responders with accurate and verifiable data regarding the location and operational readiness of emergency equipment immediately upon notification of an emergency. The invention tracks, records, and establishes workflows to maintain emergency medical equipment, such as automated external defibrillators (AEDs), by non-technical, non-healthcare providers for use by emergency responders in pre-hospital, pre-EMS medical emergencies. The unique and verifiable data obtained from this process is used as part of an emergency notification system that provides emergency responders, such as sudden cardiac arrest (SCA) responders, in an organizational setting, with immediate and accurate information identifying the nearest operationally ready medical device at the time of the emergency, which information has heretofore never been available to emergency responders such as SCA responders.

Thus, embodiments of the invention provide a bi-directional system of accountability and management, in which an emergency services provider can track the status of all its AEDs, inform users of this status, and allow the users to communicate maintenance results back to the provider. A pervasive problem in the industry is that this accountability is currently lacking. Within a given organization's emergency response team, neither the organizers nor the potential responder has any idea of the status of devices for use in an emergency, such as an AED.

Embodiments of the invention also provide a mobile application that ensures that emergency equipment, such as an AED, is verifiably physically inspected and properly maintained on a regular, e.g. monthly, basis. In this example, the information regarding location and AED operational state is captured and linked to an emergency notification application to notify SCA responders to a victim of an SCA of the location of the nearest functioning AED (see U.S. patent application Ser. No. 14/269,030, filed May 2, 2014, which application is incorporated herein in its entirety by this reference thereto).

While the invention is discussed in connection with AEDs, those skilled in the art will appreciate that the invention is equally applicable to any emergency equipment, e.g. fire extinguishers, first aid kits, etc. Further, while the invention is discussed in connection with SCAs, those skilled in the art will appreciate that the invention is equally application to any medical emergencies, as well as non-medical emergencies, and all of their specific subsets. Accordingly, the invention is not limited to AEDs or medical devices.

Overview

Central to the invention described herein is a database, maintained by an emergency services management system, which may be operated by a third party or by the emergency services provider, and containing all of the AEDs for a given site, such as a company campus. The database stores information, such as serial number, model name, location, and maintenance status. In embodiments of the invention, the database accommodates characteristics of one or more of medical equipment, supplies, medications, and non-medical equipment and/or supplies.

In embodiments of the invention, there are multiple variables in the database, such as:

1) Medical equipment, e.g. AED, stethoscope, first aid supplies, and medications.
2) Non-medical equipment, e.g. fire extinguishers, radios, NS evacuation equipment.
3) Equipment parts and accessories, such as the batteries in an AED.
4) Additional characteristics of equipment, including brand, description, different sizes, i.e. airways or gloves.
5) Expiration dates, e.g. for supplies, injury specific kits, accessories, and all medications.
6) Quantities, i.e. any supplies have variable quantities.

Each AED is equipped with a provider-supplied label or other identification token in connection with its use at the emergency services user's company site. The label contains a label that can be scanned electronically, such as a QR code, barcode, NFC or RFID tag, and the like, along with some readable text describing the AED and its location. A designated person can use the mobile app to scan the label, and thus proceed with maintenance or be apprised of any anomalies with a given AED. In embodiments of the invention, the data contained in a label comprises:

1) Provider name;
2) AED model;
3) AED serial number;
4) Battery expiration date; and
5) Pads expiration date.

Here is an example of a label:
Emergency University, Inc. Philips Onsite|4/15/2014|5/10/2014

Complex Kits

In addition to AEDs, embodiments of the invention comprehend medical and/or other complex kits, which have a variety of contents, including some requiring, some not requiring expirations, others with variable numbers, etc. To register complex kits, the database allows a selection process from a pre-developed master list, including all common types of emergency equipment, supplies, medications, kits, etc. An authorized user registers a complex kit by selecting from a master product list. The complex kit can reflect what the user already has, or what the user would like to create. The user selects from master list or adds on if an item is not on the master list. Embodiments of the invention record the contents to provide the information for periodic inspections only, or to procure user selections.

Mobile App

To facilitate AED maintenance and status reporting, the mobile app works as follows:

When the app prompts a user with "Do you Have an Emergency?" the user responds "No." At this point, if the mobile user is authorized, a screen appears with a list of AEDs in the site. Each entry in the list, populated from the aforementioned database, contains two elements: the location and the status (OK or Due) of the AED. When the user clicks on an entry in the list, an image of a camera is displayed, and the user is asked to hold the camera up to the barcode. The barcode is scanned automatically. In other embodiments of the invention, an NFC dialog, etc. may be displayed by the app.

On a successful scan, a maintenance checklist screen is displayed; this screen is specific to a given AED model, and contains a list of instructions. The user can also click on "Show Image" on the first instruction, to get a pictorial representation of the AED and how to perform maintenance.

The user clicks on the appropriate radio button when the user is ready to communicate the maintenance results to the provider. If maintenance is unsuccessful, the user must enter a description of the cause. There is also a link on the screen to telephone the provider. Once the user hits the Submit button, the results are communicated back to the provider's database via a Web service.

There are also a number of instances where a scan does not bring up the maintenance screen. These include:

The barcode is not a proprietary barcode;
There was a mismatch, e.g. the user scanned the wrong AED; and/or
The battery and/or pads have expired.

In all of these cases, the app updates the maintenance status to "Alert!" and calls a Web service to update the database to this effect. The Web service generates an email to the user indicating that the provider has been notified of the issue, and that the user is to be contacted. Note that if the scanner is unable to read the barcode, and the scanner never brings up either the maintenance screen or an error screen, then the user can hit the "Back" button. This brings up a screen that allows the user to type in the serial number, which is listed in the readable text next to the barcode. If the serial number matches a record in the database, the proper checklist screen appears, and the user can continue with maintenance.

Technical Details

FIG. 1 is a flow diagram showing a method for tracking and maintaining emergency equipment according to the invention.

In FIG. 1, a user registers for the maintenance app (100). The app communicates using a Web service with an AED program management database verifies that the registrant is an authorized AED coordinator for that facility based on first name, last name, email address and mobile phone number and maintained in an AED program management database (130).

The app starts (102). The app communicates with the server using a Web service and requests a list of facility specific AEDs based on registration data previously entered and verified in the AED program management database. The server communicates with the app using a Web service and requests a list of facility specific AEDs from the AED maintenance database. If the registrant is an authorized AED coordinator, an AED list appears. If not authorized, no AED list appears, and, instead, a "more information" screen appears (140).

The user selects "No emergency" on his device (104).

A list of AEDs is displayed (106).

The user selects an AED from the list (108). The app uses native and library code to control the device's camera function to take a picture of, for example, the QR code label on the AED (150).

The user scans the label on the selected AED (110). The app processes the label and extracts data embedded in label. The app compares the data with the AED selected from the list. If the label data matches the AED data stored in the AED program management database for the selected AED, then the app populates a custom AED inspection checklist based on the manufacturer's recommendations for that make and model. If label data does not match AED selected, then an error message appears on phone using code in the app (160), e.g. "Error Message: label does not match selected AED machine. Incorrect location or AED not registered AED program management database" (162).

The geo-location of the authorized AED coordinator is captured by the AED maintenance smartphone app when they scan the label, and the location is then reported to the AED program management database. This ensures that the AED being inspected is in the correct location and that the AED coordinator is in front of the AED at the time of the inspection (120).

Upon discovering the victim of an SCA, a bystander can initiate an emergency notification to the trained responders in their facility using an alert app, whether or not they are trained in emergency skills. The alert app and the AED maintenance smartphone app share the same database. Based on the victim's geo-location, the geo-location of the facility's AEDs, and the operational status recorded for each AED, the AED program management database determines the location of the AED that is nearest to the victim's location, and prioritizes AEDs on the basis of operational status. This allows the alert app to provide the location of the nearest functioning AED immediately to the facility's trained emergency medical responders via text message (122).

The geo-location of each AED is captured by the AED maintenance smartphone app and recorded into the AED program management database when the AED is placed into service (124).

The alert app captures the geo-location of the bystander and, by inference, the location of the victim (126).

A customized AED inspection checklist is then presented to the user (112).

The user completes and submits the AED inspection report (114). The AED program management database prioritizes the readiness of the AED into categories of: Operational; Alert pending; or Not in service, e.g. due to pad and/or battery expirations, or AED operation issues. This information is maintained along with the geo-location of the AED (128).

If user indicates that that the AED passes inspection by selecting appropriate radio button, then the app communicates with the AED program management database using a Web service and the maintenance record is updated in the AED program management database. If the AED does not pass inspection, the user indicates that the AED fails and is provided with a text field to describe the issue. In all cases of AED failure to pass inspection, the app communicates with the AED program management database, information is stored in the database, and the system sends a notification or email of the maintenance issue to responsible parties (170), e.g. "Alert!—AED requires service" (172).

The app checks the battery and pad expiration dates for the AED (116). The app compares the current date with the battery and pad expiration dates contained in label data. If the battery and/or pads have expired, the app communicates with the AED maintenance database using a Web service and the system sends a notification email of the maintenance issue to responsible parties (174), e.g. "Alert!—AED requires service" (172).

The AED program management database prioritizes the readiness of the AED into categories of: Operational; Alert pending; or Not in service, due to pad and/or battery expiration, or AED operation issues. This information is maintained along with the geo-location of the AED (128).

Central to the invention described herein is a database, maintained by the emergency services management system, which may be operated by a third party or by the emergency services provider, and which contains information for all of the AEDs for a given site, such as a company campus. The database stores information, such as serial number, model name, location, and maintenance status. In embodiments of the invention, the database accommodates characteristics of one or more of medical equipment, supplies, medications, and non-medical equipment and/or supplies.

Figure 2:
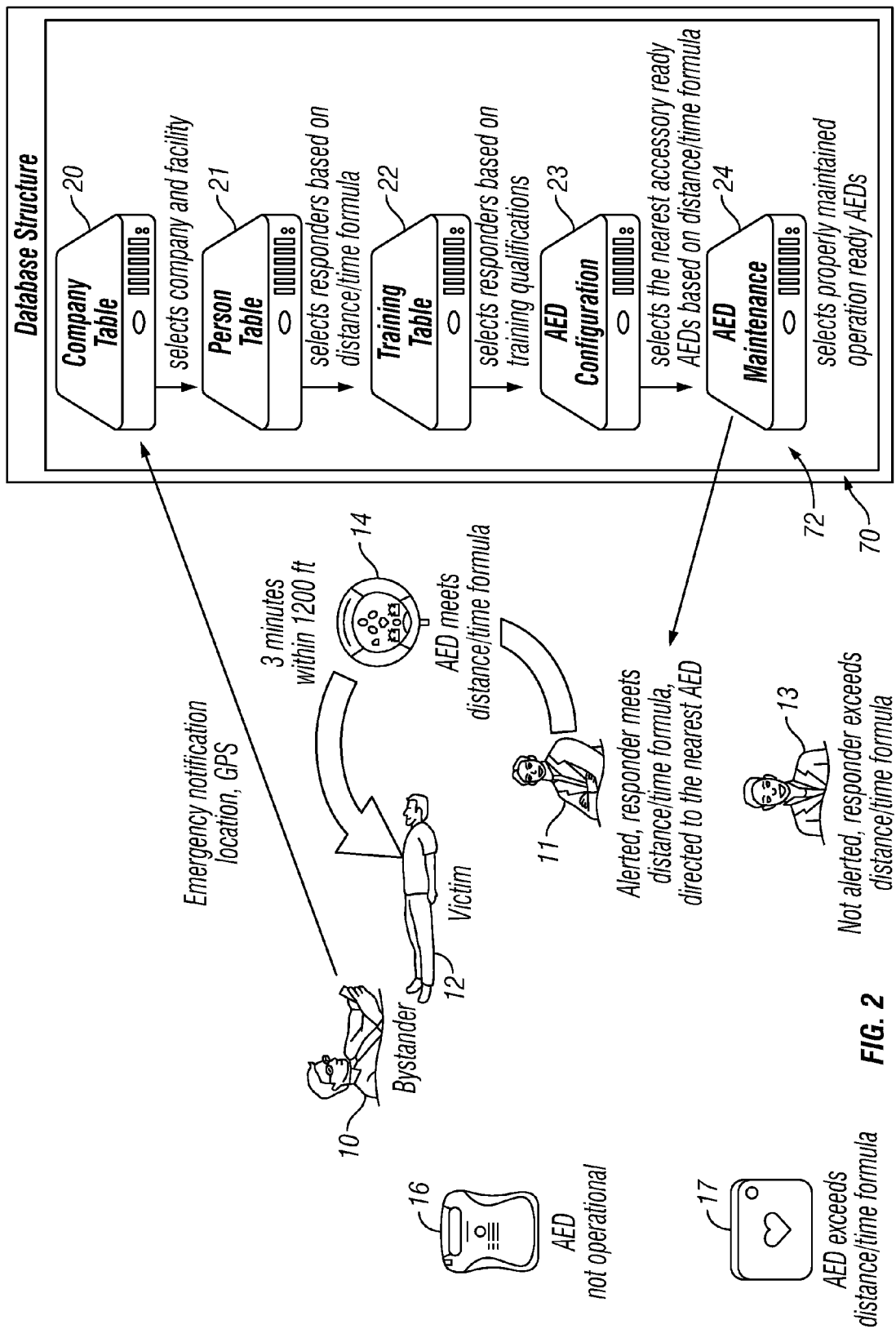
FIG. 2 is a block schematic diagram showing a system database structure according to the invention.

For example, the database has many tables, each table holding many defining characteristics, that are drawn from to make an appropriate analysis, e.g. a company table with unique company ID; a person (responder) table, each with unique person ID; multiple training tables with unique session ids; equipment configuration tables in which each piece of equipment has a specific equipment ID; and equipment maintenance tables in which each inspection has a specific maintenance ID. The following discussion describes the system database structure, as shown in FIG. 2, which is a block schematic diagram showing a system database structure according to the invention.

System Tracking of AED Locations

AEDs are recorded in the database 72 based on preconfigured company 20, AED configuration 23, and AED maintenance 24 tables.

In the company table, each parent company is assigned a unique company ID that includes defining characteristics, such as address, state, and facilities. Each facility is recorded as a sub-company of the parent company and is assigned a unique company ID associated with the parent company. The company table also includes defining characteristics for each facility, such as address, state, and GPS coordinates. The GPS coordinates of each facility (company, sub-company) are mapped based on the physical address of the facility.

In the AED configuration table, each AED is assigned a unique ID and additional defining characteristics, such as GPS coordinates, serial number, specific location in the facility, accessory expiration dates, etc. The AEDs are statically related to a company, usually a sub-company and/or facility, via a company ID. A Web-based user interface is used to register each AED, including defining characteristics, such as the specific location of the AED, e.g. kitchen, 10th floor West elevators. The specific GPS location of the AED is recorded during initial registration of the AED, when the installer is physically present at the location of installation, and is based on the geo-location of the installer's phone. In embodiments of the invention, the GPS location of the AED is re-confirmed each month during an inspection.

The AED maintenance table stores maintenance data for each AED with defining characteristics, such as the date of the inspection, whether the inspection determined the AED was operational, alerts generated, the issue generated, and the GPS location at which maintenance was performed. Each time a maintenance is performed, the record is stored in the AED maintenance table with a unique maintenance ID. The maintenance is related to an AED via its unique AED ID.

System Tracking of Responders

In embodiments of the invention, system tracking of responders involves a person (responder) table 21 and training tables 22.

Each responder is registered into the person table with a unique person ID that also includes defining characteristics, such as email and cell phone number.

Each responder is related to a facility via the company ID that is established during initial registration for training.

A separate training table is created for each responder for emergency training courses, with separate tables for online and skills completion for each course. This data is then related to the trainee via the unique person ID. Data in these tables determine which persons are the eligible responders who are to be notified in case of a particular emergency.

System Prioritizes Equipment

In operation, a bystander 10 at an emergency 12 sends their GPS coordinates via a Web-service to the emergency response notification system 70. The dynamic GPS location of the responder is obtained when a responder receives an emergency notification and indicates an intention to respond via an acknowledgement link on a mobile device.

The system prioritizes equipment and responders based on the distance/time that they are from the victim. For example, responders who are farther than three minutes away from the emergency scene are given lower priority, and are notified only after responders (and AEDs) that have the best opportunity to impact clinical outcome are notified. The notion of "nearest" responder/equipment is based on known clinical outcomes for a particular emergency based on response time. Because the distance/time element varies per emergency, a different formula for evaluation is used based on the type of emergency. In embodiments of the invention, the emergency response notification system first calculates the distance (time equivalent) between the bystander 10 and the responder 11. The emergency response notification system then calculates the distance (time equivalent) between the bystander and the AEDs located in the facility. The distance for the responder to retrieve the emergency equipment and bring it to the scene of the emergency must be less than the pre-determined maximum time allowed for the response, if the response is to be clinically efficacious. For example, for sudden cardiac arrests this time is three minutes from collapse to first defibrillation. This translates to an approximately 1000 foot round trip, i.e. running from the victim's side to get an AED 1000 feet away and return to the victim or 2000 feet one way. Embodiments of the invention consider only one way travel, i.e. the distance taken when responder runs from a current location to retrieve the AED and then runs directly to the victim.

Responders 11 are identified who are proximate to both AEDs and the scene of the emergency, such that meet the distance and time requirements 14. If the responder is identified as located sufficiently near to the scene of the emergency, then a notification is sent to the responder directing the responder to the location of AEDs that are identified as meeting the time and distance requirements. Responders 13 who do not meet the time and distance criteria are not alerted; AEDs 17 that do no meet the time and distance criteria are not considered.

Prior to sending the notification, the AEDs are assessed for their operational readiness. The emergency equipment identified as meeting the time and distance requirements is assessed prioritized based on its operational status. First, the rules engine queries the AED configuration table to assess whether the nearest AEDs selected have accessories within their expiration period. Next, the rules engine queries the AED maintenance table to determine the date of the last successful maintenance inspection and to confirm the GPS location of the AED.

The rules engine establishes a prioritized list of available AEDs as follows:

Priority 1. Emergency equipment that has been inspected and deemed operational within past thirty days, whose location has been confirmed, and for which all accessories are within a recorded expiration period.

Priority 2. Emergency equipment that has been inspected and deemed operational within past sixty days, whose location has been confirmed, and for which all accessories are within their recorded expiration period.

Unavailable emergency equipment 16. A designation of non-compliance is rendered under the following conditions and the AED is not provided as a selection to the responder if:

Upon query of the AED configuration database, the equipment has expired accessories; and/or Upon query of the AED maintenance database, the equipment has not been inspected and deemed operational and/or whose location has not been confirmed within the past sixty days.

Those skilled in the art will appreciate that the foregoing discussion provides an example of the invention used in connection with AEDs. The invention is applicable to any other type of emergency equipment. Further, the intervals for inspection, etc. are provided in view of a presently preferred embodiment of the invention. Thus, other intervals for inspection can be established as appropriate.

Replacement of Accessories

Figure 3:
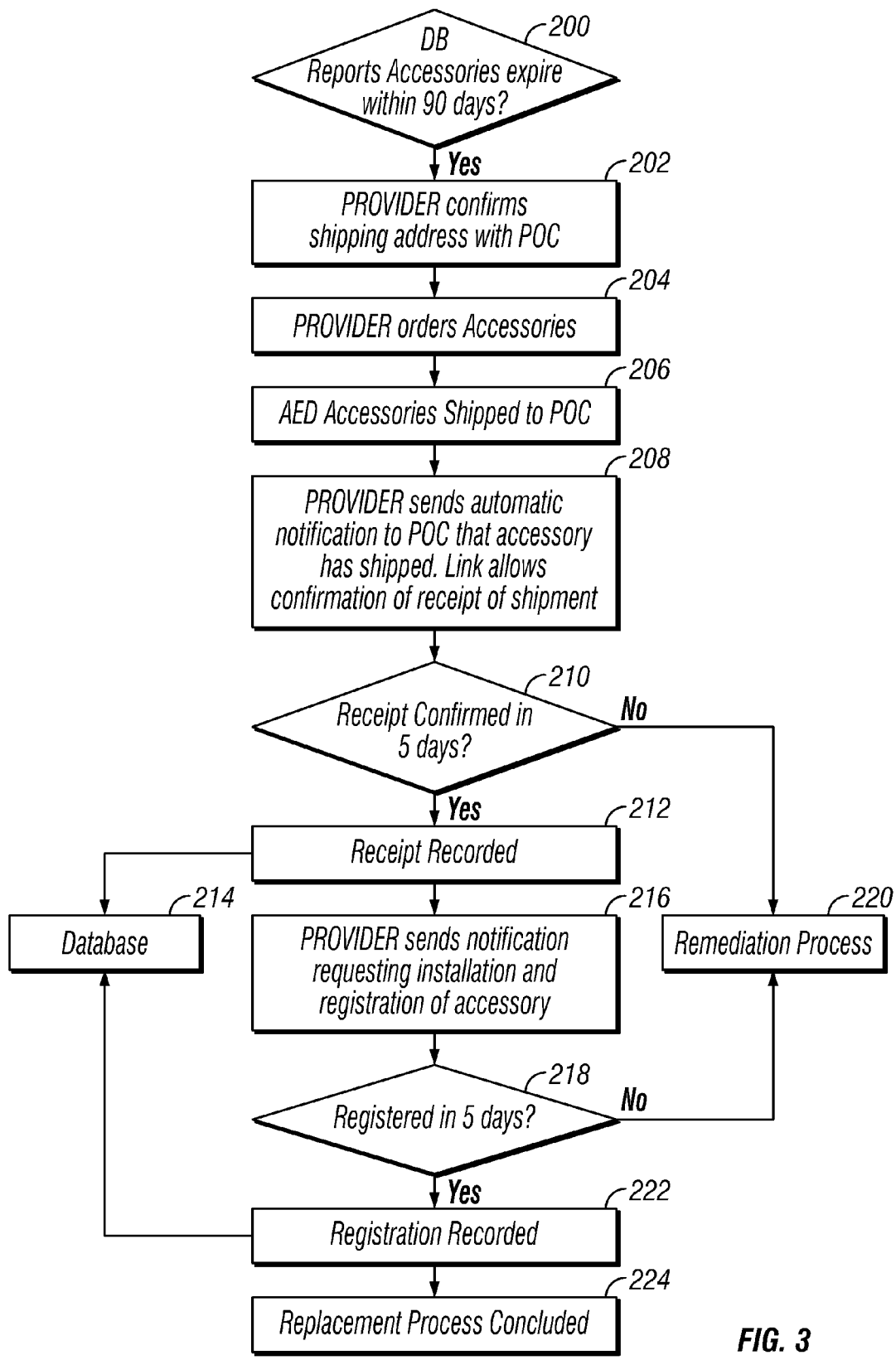
FIG. 3 is a flow diagram showing a method for replacement of accessories according to the invention.

FIG. 3 is a flow diagram showing a method for replacement of accessories according to the invention. In FIG. 3, the database reports that a battery or pad is about to expire, e.g. within 90 days (200). An emergency services management system confirms the shipping address with the point of contact (POC) (202) and orders the battery and/or pads from the provider (204). The AED and/or pads are shipped to the point of contact (206) and the emergency services management system sends an email to the point of contact indicating the accessory has shipped (208). An email links allows confirmation that the message has been received. A determination is made is the receipt is confirmed, e.g. within five days (210). If confirmation is not received within the allotted time, the a remediation process begins (220). If confirmation is received within the allotted time, then the receipt is recorded (212) and stored in the database (214). Thereafter, the emergency services management system sends an email notification requesting installation and registration of the accessory (216). If a registration is received within a predetermined time (218), i.e. five days, then the registration is recorded (222) and stored in the database (214) and the replacement process is concluded (224); else, a remediation process is commenced (220).

Remediation

Figure 4:
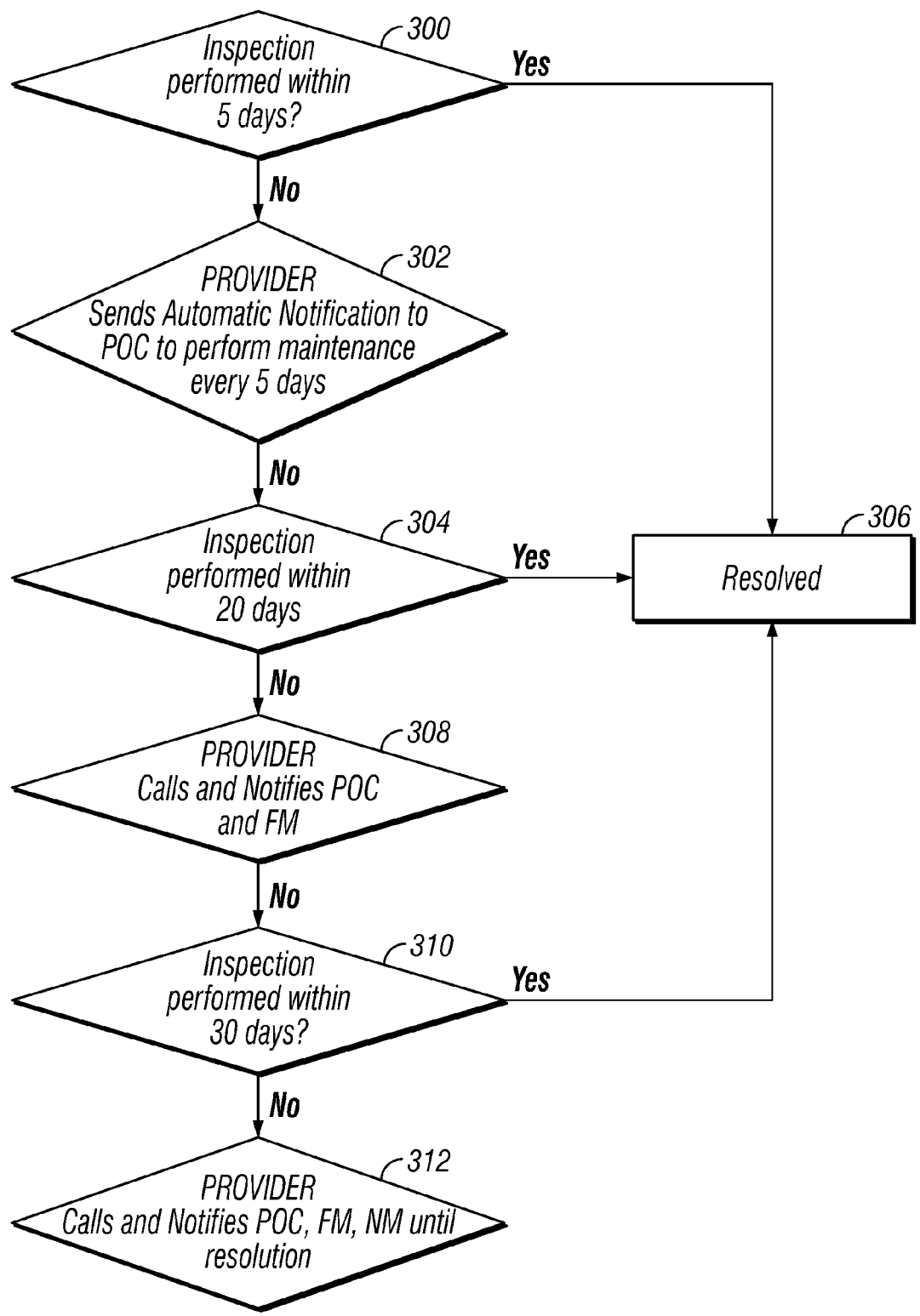
FIG. 4 is a flow diagram showing a method for remediation according to the invention.

FIG. 4 is a flow diagram showing a method for remediation according to the invention. In FIG. 4, a check is made to determine if an inspection is performed within a predetermined time after it is ordered, e.g. five days (300). If the inspection has been made within the allotted time, then the maintenance request is resolved (306); if not, then an automatic notification is sent to the point of contact to perform maintenance every five days (302). A further check is made to see if the inspection is performed within a further interval, e.g. twenty days (304). If the inspection has been made, then the maintenance request is resolved (306); if not, the management service calls and/or emails the point of contact and the site administrator (308). A further check is made to determine if the inspection has been performed within a yet further interval, e.g. thirty days (310). If the inspection has been performed, the maintenance request is resolved (306); else, the management service calls and emails the point of contact, site administrator, and the national program manager (NPM) until resolution is confirmed (312).

AED Replacement

Figure 5:
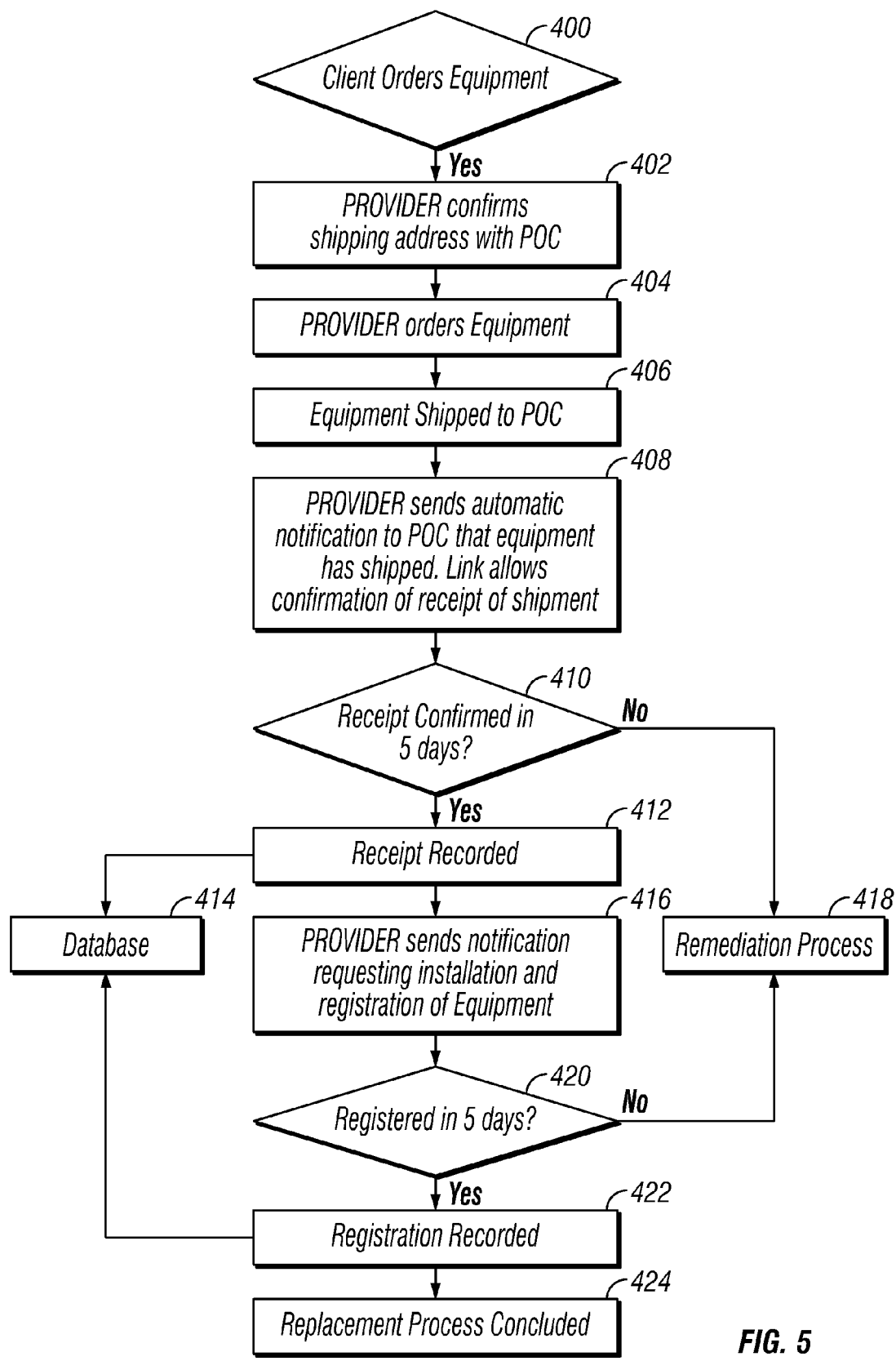
FIG. 5 is a flow diagram showing a method for a new or replacement AED ordered by a client according to the invention.

FIG. 5 is a flow diagram showing a method for a new or replacement AED ordered by a client according to the invention. In FIG. 5, a client orders an AED (400). The emergency services management system confirms the shipping address with the point of contact (402) and then orders the AED from the provider (404). The AED is shipped to the point of contact (406). The emergency services management system sends an email to the point of contact confirming that the AED has shipped (408). An email link is included to allow confirmation of receipt of the shipment. A check is made to see if the shipment is received within a predetermined amount of time, e.g. five days (410). If the shipment is not received, a remediation process is started (418). If the shipment is received, then the receipt is recorded (412) and stored in the database (414). The emergency services management system sends an email notification requesting installation and registration of the AED (416). If the AED is registered within a predetermined period of time, e.g. five days (420), then the registration is recorded (422) and stored in the database (414), after which the replacement process is concluded (424); else, a remediation process is commenced (418).

AED Maintenance

Figure 6:
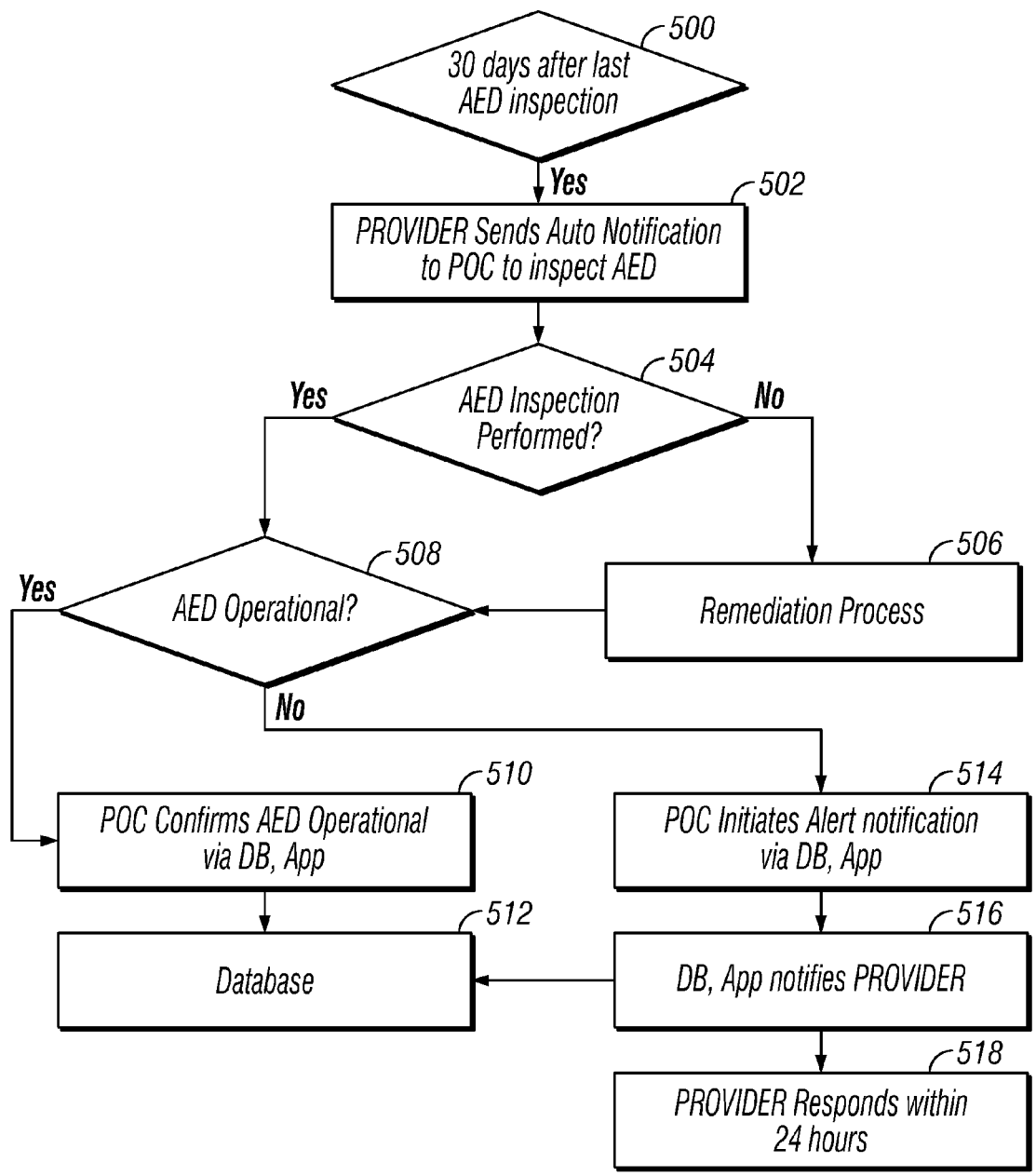
FIG. 6 is a flow diagram showing a method for AED maintenance according to the invention.

FIG. 6 is a flow diagram showing a method for AED maintenance according to the invention. In FIG. 6, a determination is made if a predetermined amount of time has passed since a last inspection, e.g. thirty days (500). If this time has elapsed, then the emergency services management system automatically sends an email to the point of contact asking that an inspection be made (502). If the inspection is made (504), the a determination is made if the AED is operational (508). If the AED is operational, then the point of contact confirms that the AED is operational via an alert (510) and the alert is saved in the database (512). If the AED is not operational, then the point of contact sends an alert notification (514) and the alert system notifies the AED program manager (516) and the alert to the AED program manager is saved in the database (512). The AED program manager then responds within 24 hours (518). If the inspection is not made (504), then a remediation process is commenced (506). When the remediation process is resolved, the process proceeds to determine if the AED is operational (508), as discussed above.

System Components and Operation

Figure 7:
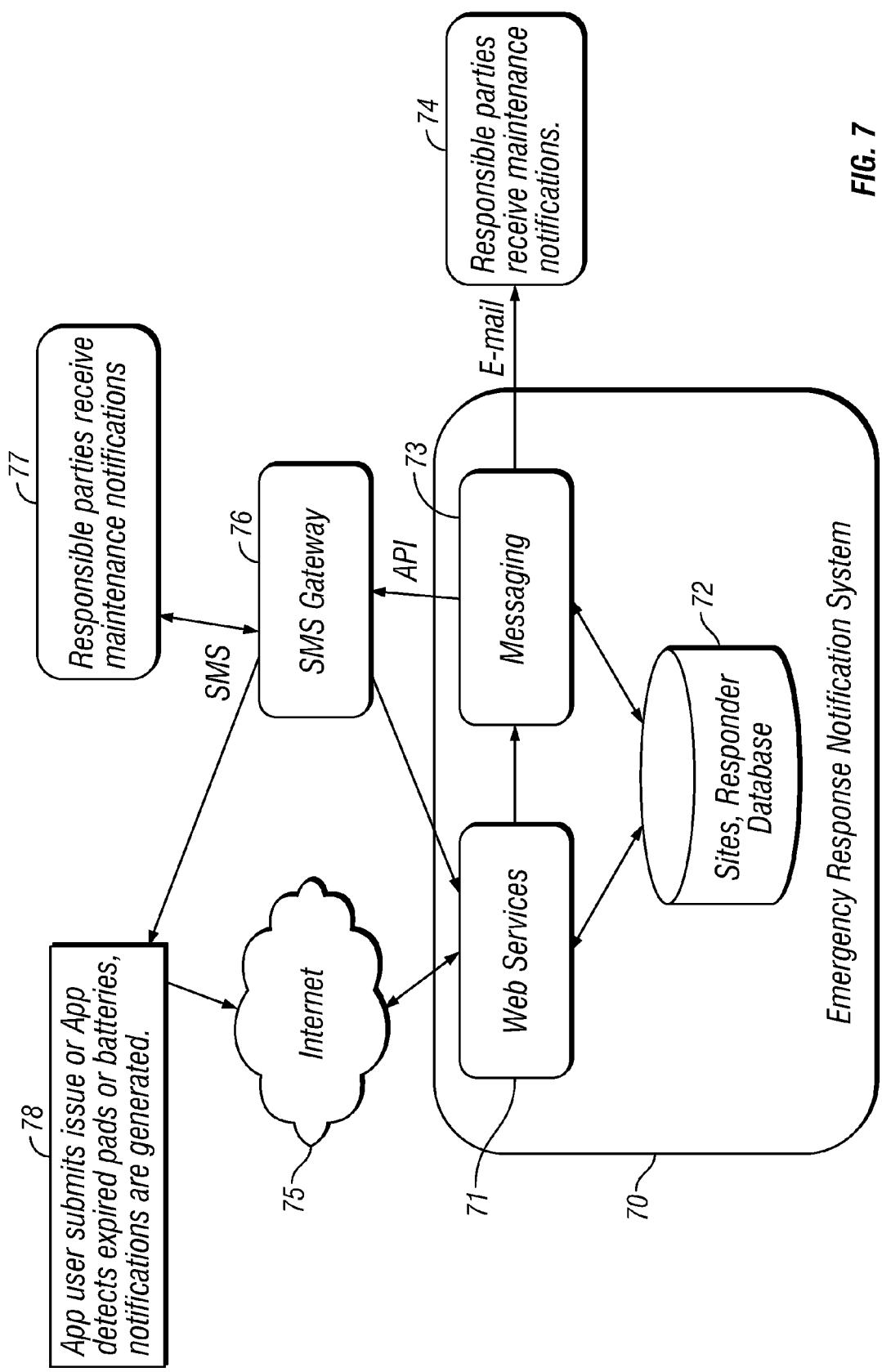
FIG. 7 is a block schematic diagram showing a system for tracking and maintaining emergency equipment according to the invention.
Figure 9:
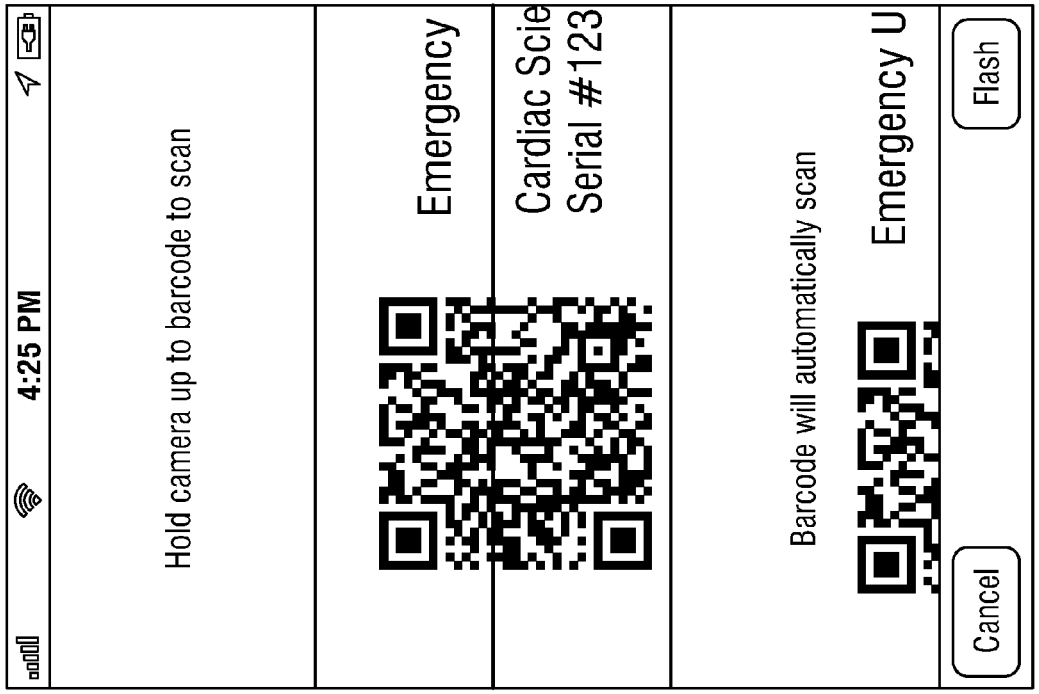
FIG. 9 is a screen shot showing AED barcode scan according to the invention.
Figure 8:
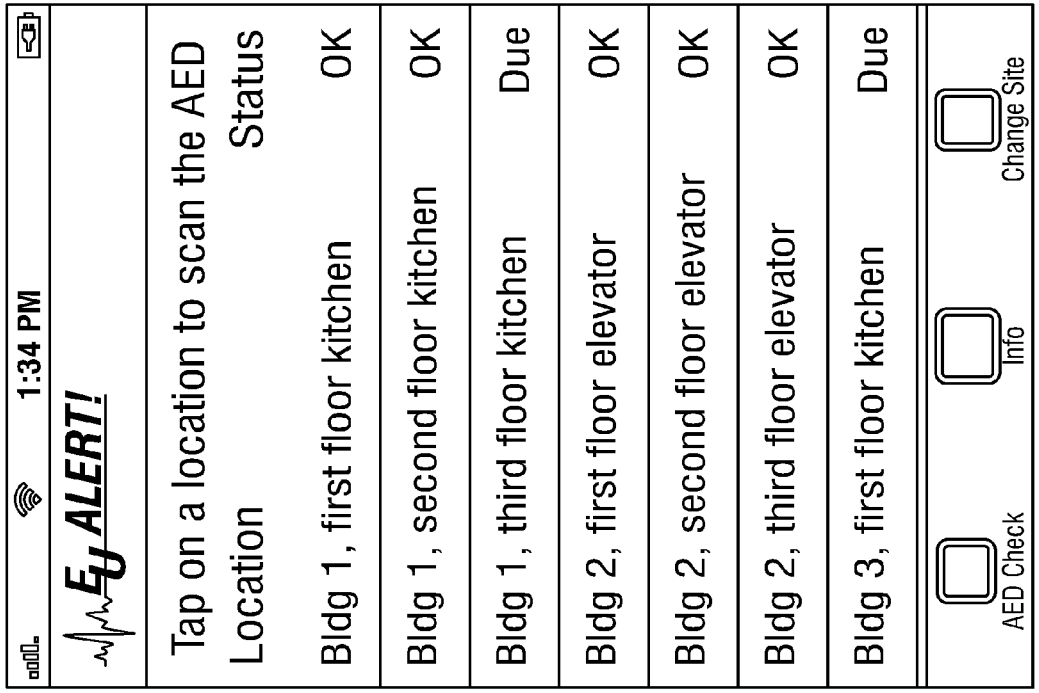
FIG. 8 is a screen shot showing AED locations according to the invention.

FIG. 7 is a block schematic diagram showing the main components of a system for tracking and maintaining emergency equipment according to the invention. These components include a database 72 that stores data acquired through management applications; a rules engine 70, including a learning management system that acquires and hierarchically stores raw data and that analyzes the data based on rules; a multi-mode, multi-dimensional communications, and two-way messaging and communication system 73, including emails, an SMS gateway 76, telephone and intelligent communications to provide progressive levels of intelligence, analyzed information, and compiled information that is dynamically driven by the rules engine, and including a mechanism for sending and receiving both human-to-human and technology generated intelligence, e.g. two-way communications and content between system participants, such as a responsible party 74, 77; Web services 71 which communicate via the Internet 75, including business logic that performs functions directly on the database, initiates communications, provides analysis, and compiles reports; a mobile application 78 that provides an access point to the system and/or user interface and geo-location capabilities.

In embodiments of the invention, a communication mechanism between the mobile app and the provider's database is in the form of RESTful Web services (REST, short for Representational State Transfer, is a stateless, resource-oriented client server model that makes explicit use of HTTP methods). The data transfer protocol is JSON (Java Script Object Notation); the mobile app sends request data in this format, and parses the similarly formatted response data. In embodiments of the invention, there are three Web services that make up AED maintenance: the AED list service, the AED maintenance service, and the AED error service.

After initial registration has been started, the app invokes the AED list service. This service runs asynchronously because the user should not experience any apparent delays while the app is running. This service is also called when the app is restarted by the mobile operating system; because cell phones are constantly pausing, resuming, and restarting apps, this insures that the user sees the latest state of the database. The list service takes a facility id, and an authorization as input. Not everyone in an organization has AED maintenance privileges and, therefore, the authorization scheme serves to prevent the AED list from displaying for those users. For those users with the proper authorization, the AED list is populated with records from the database.

When the user clicks on a given row in the AED list, the app brings up the scanner. In embodiments of the invention, the software library for the scanner is an open source library called ZXing.Net.Mobile, which is based on the ZXing library (pronounced Zebra Crossing). The app scans the barcode, and if the scan is successful, it parses the information it retrieved, and saves the various pieces internally. It does sanity checks, and if there are errors, such as a battery and/or pad expiration date is earlier than today or there is a mismatch of some kind, then the app puts up an error screen, and calls the AED error service (discussed below).

As previously mentioned, on a successful scan, the user sees the maintenance checklist. Once maintenance is performed, either successfully or not, the user clicks the Submit button, which calls the AED maintenance service. The app passes the following parameters to the AED maintenance service:
  Authorization
  Id (internal database id for a given AED)
  Whether or not the maintenance was successful
  Whether the battery had expired
  Geo coordinates (latitude and longitude of the user's location)
  Message (if unsuccessful, the user needs to include this it appears in the error email)

The database is updated based on these values. In the case of a maintenance error, the AED maintenance service generates an "AED Alert Confirmation" email. The email contains information about who reported the error, in which site the error occurred, the location where the error occurred, and the error message that the user entered in the app. In the case of scanning error, e.g. not a proprietary barcode, scanning mismatch, or component expiration, the app calls the AED error service. The error service accepts the following parameters:
  Authorization
  Site id
  Id (same as above—the database id)
  Geo coordinates (latitude and longitude of the user's location)
  Serial number (if applicable)
  The revision of the app
  Message (generally the same message the user sees on the app's error screen)

No database update happens here, but the error service generates an AED maintenance error report email, which is sent to both the provider and the user. The email contains information about who reported the error, in which site the error occurred, the app revision, and the error message.

The AED maintenance smartphone application uses a secure database that maintains a hierarchy of facilities, responsible parties, and AED asset data. For each AED, the data maintained includes, for example:
  1) Manufacturer name;
  2) Make and model of the AED;
  3) The location where the AED is installed;
  4) The serial number of the manufacturer;
  5) Pad and battery expiration dates;
  6) Pad lot numbers;
  7) In service date, i.e. the date the AED was placed in service;
  8) The date of the last physical inspection;
  9) Operational status of the AED; and
  10) The contact information for the responsible party at that facility, including first and last name, phone number, email address, and physical address.

An electronically readable label, such as a QR code, barcode, NFC or RFID tag, is placed on each AED and/or AED cabinet when each machine is installed. The label contains essential AED asset data that can include any asset data stored in the database, including for example serial number, location, make, model, and pad and battery expiration dates. Identifying text is also printed on the label to assist with immediate identification, such as location, make and model, and serial number. The text serves as a failsafe if the label is not readable.

AED coordinators, responsible for AED maintenance at their facility, download the AED maintenance smartphone application from, for example, the Android® or iPhone® app stores onto their smartphones. The AED coordinators register using their organization's predetermined code. Next, they localize themselves into their facility, which is facilitated by a drop down menu. Additionally, the AED coordinators enter their smartphone telephone number, which is then stored in the database. The database recognizes the user as being authorized or not authorized to view and manage AEDs at their facility based on their first name, last name, and email address. The AED coordinator's authorization and list of AEDs is linked to their smartphone number. No individual, except the responsible party has access to that list, either in the database or on their smartphones. In embodiments of the invention, authorized users may include a single person per facility, one person may be authorized for multiple facilities, and any number of persons may be authorized for any number of facilities, as desired.

To perform an inspection, the inspector must be pre-authorized by his organization. Hierarchical access to information is recorded in the database. Otherwise. the inspector cannot receive any object data. While the primary storage of all equipment related location, characteristics and operational status data is located on a database server, the authorized inspector maintains a local cache of data on his mobile device relating to objects under his authorization, that is periodically synched with the database.

On a periodic, e.g. monthly, basis the AED program management system sends the AED coordinator an email notification and a text notification to complete the required AED maintenance. The mobile application adds an important layer of accountability to the currently available AED program management systems. Instead of an unverified reply to an electronic message, the AED maintenance smartphone application verifies that the AED coordinator is physically present at the AED's location. Specifically, the mobile application requires the responsible party to scan the QR code that has been placed on the AED and/or its cabinet.

Upon receiving notification to perform maintenance, the AED coordinator opens the mobile application. An authorized AED coordinator then views a display of their AEDs, listed by location.

The AED coordinator travels to one of the AED locations displayed on the screen. The user selects an AED by clicking on its location. Upon clicking on the AED, a scanner pops up and allows the AED coordinator to scan the QR code. If the QR code matches the expected data in the AED management database, a brief inspection procedure appears on the mobile application. The inspection procedure is customized to meet the requirements of each manufacturer's make and model. The app includes clickable custom images to assist the AED coordinator to properly find, view, and interpret the ready light. The inspection of the ready light indicates that the AED is or is not working properly based on its daily self checks.

Once the inspection procedure appears, the AED coordinator completes the process displayed on the screen and has two options depending on the inspection's outcome. The AED Coordinator can either:

1) Click a radio button that indicates that all inspection and/or maintenance requirements are met; or 2) Click a radio button that indicates that some requirements are not met.

If the requirements are not met, the AED coordinator is prompted to type in a brief description of the problem, and then submit a request for assistance. The AED coordinator's request for assistance is immediately uploaded to the AED program management database, and provided as an alert to the AED program management vendor who monitors the AED management program.

If an alert is received, AED personnel from the organization's AED management program service provider call the AED coordinator within, for example, 24 hours to assist with the detected AED issue. In addition to sending a request for assistance, the AED coordinator may call directly from the mobile application if a problem is detected that requires immediate attention.

If the label does not match, the user is informed that the AED present at that location is either:

1) In an incorrect location, and the user is then provided with the correct location; or 2) Is not registered in the database.

An alert notification is sent to the organization's AED management program service provider. The user is given the option of calling the AED management program service provider directly from the application, or receiving assistance initiated by the AED program management service provider within the next, for example, 24 hours.

Scanning the label, a requirement for completing the maintenance, provides true accountability that the AED coordinator has actually physically attended and inspected the AED. If the AED coordinator fails to scan the label, complete the inspection checklist, and click the appropriate radio button indicating the status of the AED, then the AED program management database continues to display the AED's status as "Due" and still requires maintenance.

When AED maintenance has not been performed within the prescribed time period, a member of the responsible vendor team of AED program specialists calls the AED coordinator directly and repeatedly until maintenance has been completed.

In addition, the AED coordinator continues to receive notification emails and texts until the required maintenance is performed. If the AED coordinator cannot be reached within a prescribed period of time, the AED program specialist contacts the responsible organization's AED program manager to determine whether the individual is still at the facility, or whether a new AED coordinator must be appointed and educated about the process.

An additional feature of the mobile application is the ability to communicate status and requirements with other departments or personnel involved in an organization's AED management program. AED alerts can be sent to:

1) The purchasing agent to prompt ordering and shipping new replacement parts, e.g. for expired pads and batteries;

2) The manufacturer, to maintain surveillance on their AEDs;

3) The AED management program service provider who manages the AED program;

4) The organizational managers, to ensure that they are aware of the status of the AEDs in the company; and 5) The AED coordinator, to confirm that any issue they have identified is being addressed.

Prior to this mobile application, no mechanism existed to ensure the accountability that those charged with AED maintenance actually perform the required physical inspections. Nor has there been a mechanism that accurately records and reports the correlation between the physical location of the AED, its serial number, and pad and battery expirations.

Geo-Location

The geo-location of each AED is captured by the smartphone app and recorded into the database when the AED is placed into service. The geo-location of the responsible party is captured from their smartphone when the label is scanned, and then reported to the database. Embodiments of the invention verify that visual inspection has actually been performed for the AED that is expected to be at that location.

The ability to locate AEDs precisely assists manufacturers of AEDs to locate AEDs that are under FDA recall. The FDA issues recalls when it determines that there is sufficient evidence to conclude that certain AEDs are defective requiring repair or replacement. Since 2005, there have been 68 AED recalls, including 17 Class I recalls (most severe warnings), affecting 385,922 AEDs. It has been difficult if not impossible for OEMs to repair and replace many of these AEDs due to poor tracking of critical location data.

Because the important responsibility of maintaining functioning AEDs is assigned primarily to volunteer members of the workforce, the app was designed to be simple to use, have a clear and user-friendly interface, and must minimize the time required to perform maintenance. The automated reporting feature allows the mobile application to report directly to the database, as well as to parties who are responsible for resolving outstanding issues. The app enhances communication between responsible parties, and ensures accurate recording of the status of AED assets.

The mobile application must be supported by knowledgeable personnel, who timely deal with AED issues that are identified, and a strict regimen of personal follow-up must occur, when maintenance is not performed.

Different mechanisms can be used to ensure that the inspector is geographically located near the object, e.g. the AED, requiring inspection and that the object is the intended object. In embodiments of the invention, a mechanism is used that ensures that the inspector who is assessing operational condition is geographically located near, and is hierarchically authorized to inspect the device and/or object that requires periodic inspection.

When responding to an emergency, the location of the object is provided to responding user including, for example, its text location, its location on a map, its location on a blue print, with guidance such as Waze, with step-by-step directional assistance, with a GPS image, with voice prompts, etc.

Objects

While the discussion herein concerns an embodiment of the invention that is concerned with AEDs, the invention has broad applicability to any emergency and/or medical equipment, supplies, etc. The equipment, supplies, etc. are referred to generically herein as "objects." The object is an item or information, or anything else that is required during an emergency. During medical emergencies, the object can be an AED, a first aid kit, a medical kit, medication, injury specific kits, gurneys, stretchers, splints, other medical supplies, or any piece of emergency medical equipment, supply, or medication. During a non-medical emergency, an object can include a fire extinguisher, evacuation equipment, such as stair chairs, radios, other communication equipment, vests, flags, bullhorns flashlights, search and rescue equipment, etc.

In embodiment of the invention, information is gathered from the periodic inspection. A primary purpose of confirming geographic location and operational status is to provide an object during an emergency to responding emergency personnel.

A primary purpose in gathering and ensuring the operational status of the object is to provide the location and operational status of the equipment to responding emergency personnel in a workplace. Relying on an emergency app, such as the EU-Alert app, the location and operational status of the equipment is communicated via, for example, text, SMS, voice, etc., to a layperson responder in a workplace who is notified of an emergency and then responds. The emergency responder often needs to bring medical equipment or other emergency equipment and/or supplies to the emergency, and can be informed immediately of such object's confirmed location and its operational status.

The equipment is selected based on the type of emergency, the role of the responder, the actions specified by the organization's emergency response plan, and then assessed by a rules engine as to its operational status. The object is selected based on its proximity to the emergency and the particular emergency responder who has acknowledged that he is responding.

The operational status is determined by preconfigured rules that ensure that the responder is not directed to equipment that has not been confirmed as being in a specific location, or that has not been recently inspected, or that has expired accessories, or that has been determined to have an issue pending resolution.

Registration of the Object at its Point of Installation

During the initial installation of the object, the authorized individual registers the object at its intended, static location. Registration includes a text description of the location. Additionally, the user's mobile device establishes the GPS or other electronically determined geo-location of the device. Subsequent inspections rely on either, or both of, the text description of the location and the recorded GPS location.

A mobile device, e.g. a smartphone, etc. locally stores the pre-configured specific location of the object, e.g. emergency response equipment, supply, medication, tool, etc., as well as its registered characteristics. These characteristics can include serial number, equipment type, brand, description, location, point of contact, expiration dates, last use, etc.

The inspector receives a periodic notification, e.g. via text, SMS, or email, to inspect the object. The inspector, who is authorized by the database, is provided with information regarding the locations of the objects to be inspected on the user's app interface, for example building 10A, fifth floor conference room. Upon reaching a selected object. The mobile device confirms the GPS location of the inspector and the GPS location of the object. The authorized user is presented with the pre-established inspection tool, dependent on the object type, brand, etc. The data includes expiration of the object or its accessories, supplies, or medications; the quantity; the contents if a kit; last inspection date; and operation status prior to current inspection.

Embodiments of the invention also provide for the automatic procurement of a series of shipping, receipt installation, and/or confirmation emails. Thus, when maintenance is performed and content expires, a series of emails is triggered, for example, because the AED pads have been ordered. This lets the coordinator know that such supplies, etc. are to be replaced, depending on who places the order for such supplies, and allows the order and its progress to be tracked in connection, for example, with the replacement supplies.

In another instance, the relationship between the inspector and the object is established using i-beacon technology attached to the object that communicates with the mobile device, with or without GPS. Alternatively, the relationship between the inspector and the object is established using any of NFC technology that communicates with the mobile device; object scanning and/or recognition software, with or without GPS; barcodes and/or QR codes affixed to the object, with or without GPS; and RFID or audio and/or light sensors that are part of, or attached or affixed to, the object, with or without GPS.

Periodic Confirmation of Location and Operational Status

The location of the equipment is confirmed periodically, most commonly monthly, that it is located where it was registered, or where it was officially moved to and re-registered. This ensures that emergency responders do not try to retrieve equipment that has been moved or that has operational problems. If necessary, the emergency responder can then be sent to other equipment, supplies, etc.

Another purpose of confirming geographic location is to detect equipment that has been moved, taken out of service, or that is otherwise not in the anticipated location, and then to remedy the situation.

Another purpose for confirming operational status is to resolve the issue and make the unit operational again, for example if the object requires replacement of accessory parts. Otherwise, at the time of an emergency, the object is found to be defective or non-operational, or the contents of the object are found to have been used and require replacement. In such cases, the inspector can send an alert stating that the inspection did not meet its requirements, and some requirement must be addressed.

Embodiments of the invention provide for brand specific checklists, images, and/or prompts. For example, brand specific maintenance checklists and information are provided for AED's and other equipment and contents of equipment, e.g. an AED manufacture specific maintenance checklist is pro vided as per the manufacture's recommendation, in which the images can be brand specific.

Also included are tutorials for how to perform variety of maintenance task as appropriate, e.g. a tutorial on how to use the app and/or brand specific instructions on how to install any replacement accessories.

Use to Mitigate Sudden Cardiac Arrest Events

The mobile application herein disclosed provides detailed information regarding the operational status of the AED to the AED program management database. This allows the database to prioritize the readiness of the AED into categories of:

1) Operational;
2) Alert pending; or
3) Not in service, e.g. due to pad and/or battery expirations, or AED operation issues.

This prioritization allows an emergency alert system, such as EU Alert, to notify trained responders to an SCA of the location of the nearest functioning AED, based on a hierarchy of readiness, which is a process that does not exist in any other system.

Upon discovering the victim of an SCA, a bystander (whether or not they are trained in emergency skills) can initiate an emergency notification to the trained responders in their facility using EU Alert. EU Alert captures the geo-location of the bystander and by inference the location of the victim. The AED maintenance app captures the geo-location of each AED and stores the information in the AED program management database. In embodiments of the invention, EU Alert and the AED maintenance smartphone application share the same database. Based on the victim's geo-location, the geo-location of the facility's AEDs, and the operational status recorded for each AED, the AED program management database determines the location of the AED that is nearest to the victim's location, and prioritizes AEDs on the basis of operational status. This allows the EU Alert app to provide the location of the nearest-functioning AED to the facility's trained emergency medical responders immediately via text message.

App Tutorial

The following, in connection with FIGS. 3-11, describes the user interface of the app.

1) Title: AED Locations

Content: By selecting "no" when the application asks, "do you have an emergency" the user presented with a screen that lists the locations and status of each AED of the site to which he is currently registered. To initiate a barcode scan of a single AED, the user taps the location of the designated AED and a barcode scan option appears. If the user's site does not have any AEDs, there is not a list. (see FIG. 8)

2. Title: AED Barcode Scan

Content: Using the smartphone's built in camera, the user aligns the barcode sticker on the AED machine with the camera and the barcode is automatically scanned. When the scanner succeeds, it presents a maintenance checklist for that AED. (see FIG. 9)

3. Title: AED Checklist

Content: To complete the maintenance check for the AED that has been scanned, the user scrolls through the checklist and selects one of the three options. Once the user has selected the correct option, the user presses the green "submit" button to send the maintenance report. If not all conditions are met while going through the checklist, the user selects the third option and uses the blank data field to describe the problem before pressing the green "submit" button. (see FIGS. 10 and 11)

4. Title: Show Image

Figure 12:
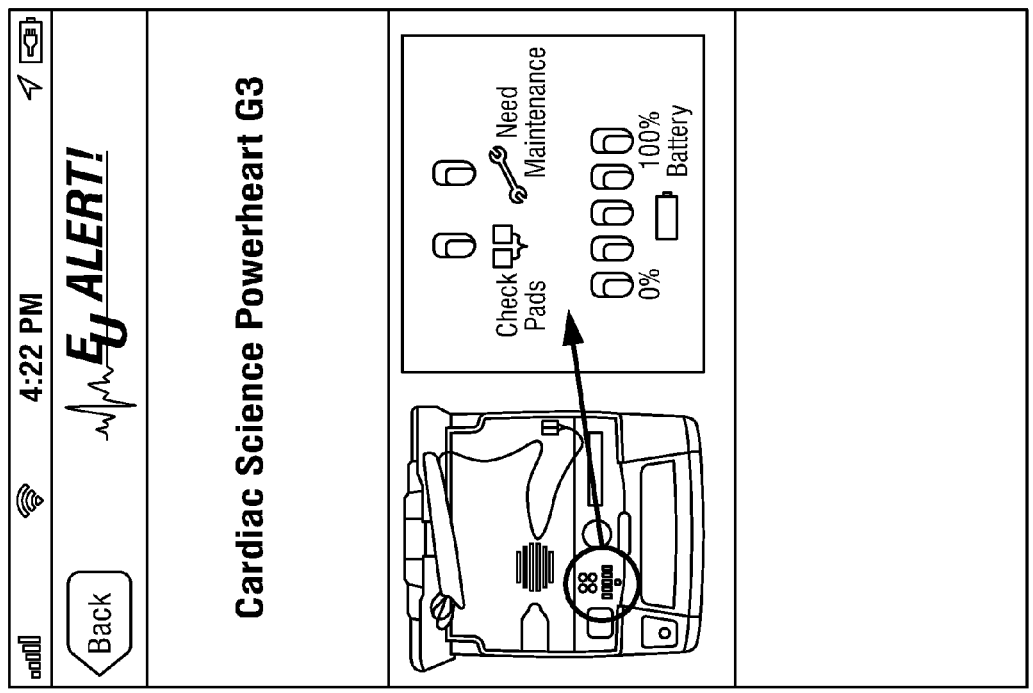
FIG. 12 is a screen shot showing an image according to the invention.

Content: On the first page of the AED checklist there is a link titled "show image" By opening this link, the user is shown a picture of the AED that has been scanned that diagrams what the user is looking for while going through the checklist. To return to the checklist, the user presses the blue "back" button in the top left corner of the screen. (see FIG. 12)

5. Title: Unable to Read Barcode

Figure 13:
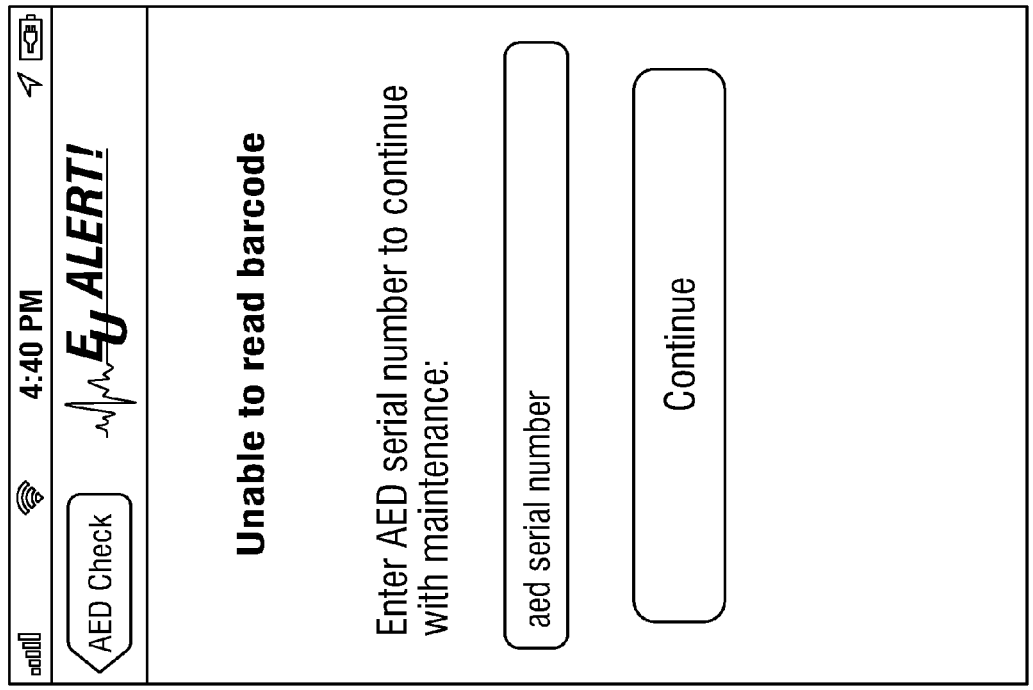
FIG. 13 is a screen shot showing a failure to read a barcode locations according to the invention.

Content: If the user attempts to scan the barcode of an AED and the scan fails or canceled, the user is taken to a screen titled "unable to read barcode." To access the AED maintenance checklist for the AED that was to be scanned, the users use accesses data field to input the serial number of the AED manually and presses the green "continue" button to proceed to the checklist. (see FIG. 13)

6. Title: AED Scan Mismatch

Figure 14:
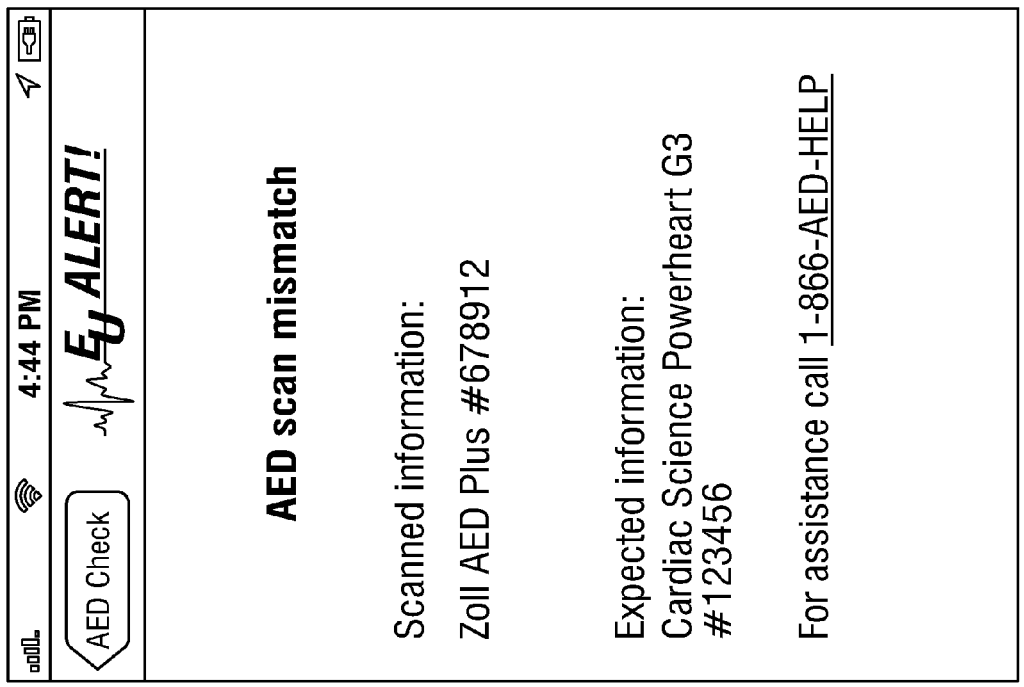
FIG. 14 is a screen shot showing an AED scan mismatch according to the invention.

Content: If the user has selected an AED from the location list and the scan of the barcode for that AED does not match the original selected location, the user is taken to the error screen in FIG. 14. To rectify the situation, the user is asked to call the number listed in the screen.

7. Title: Information

Figure 15:
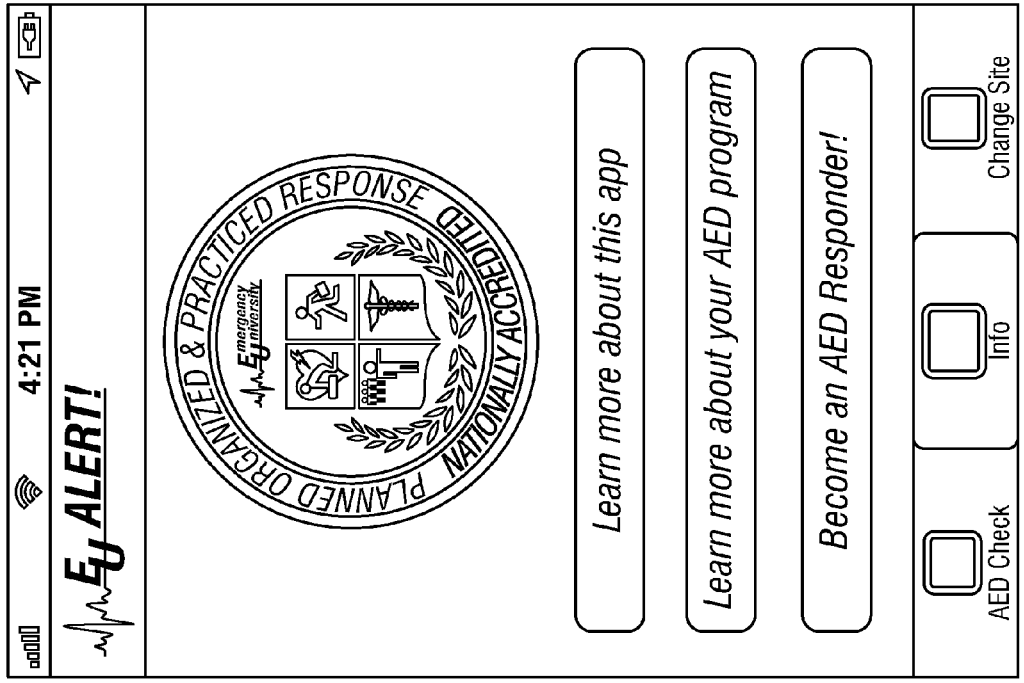
FIG. 15 is a screen shot showing information according to the invention.

Content: If the user selected the middle icon at the bottom of the AED location screen titled "info," the user is taken to the screen shown in FIG. 15. This screen gives the user three options, which are to learn more about the app, learn more about the AED program, and an option to become an AED responder if the user is not already certified as one.

8. Title: Change Site

Figure 16:
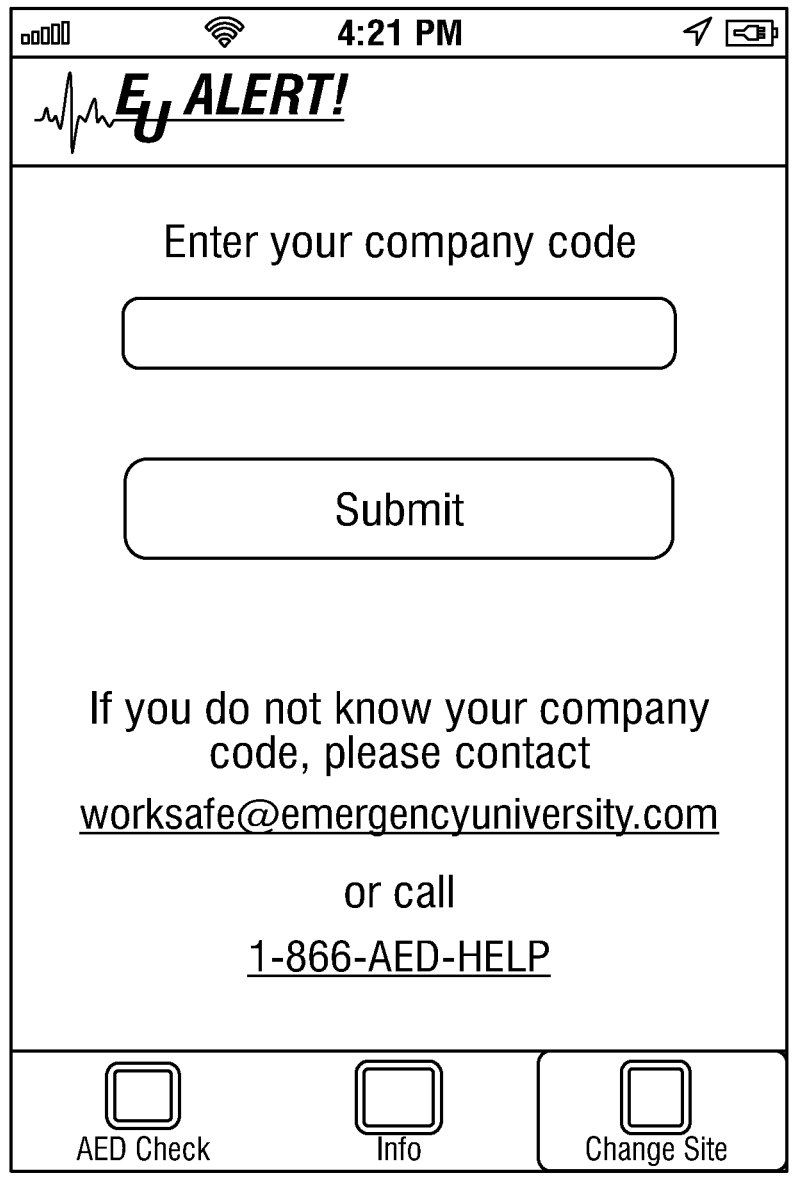
FIG. 16 is a screen shot showing a site change according to the invention.

Content: If the user has selected the "change site" icon in the bottom right corner of the AED location screen, the user is taken to the screen shown in FIG. 16. To change the site, the user must enter the company code of the site at which he is trying to reregister. If the user does not know the company code, the user is asked contact Emergency University using the options listed in the screen.

Computer Implementation

Figure 17:
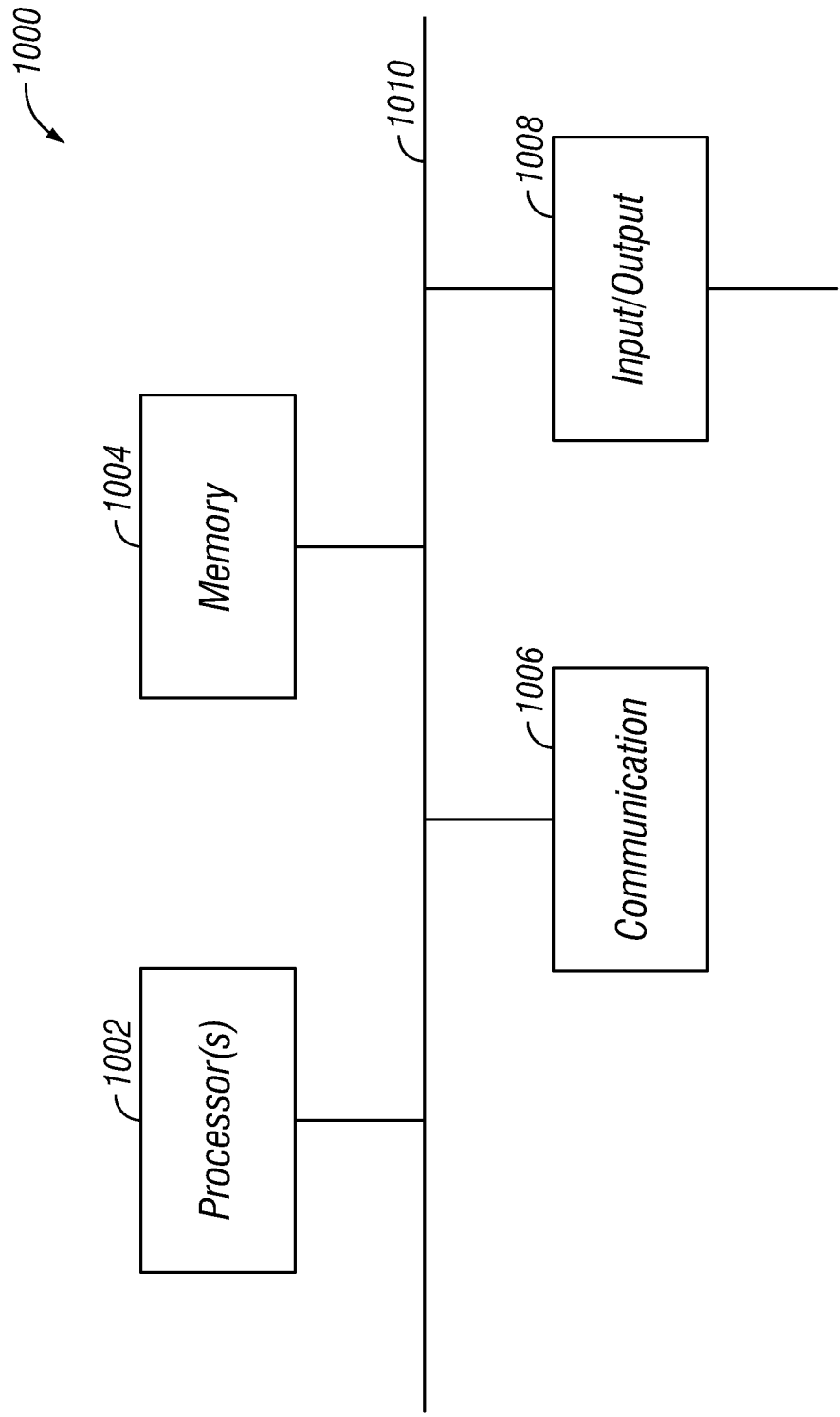
FIG. 17 is a block schematic diagram showing a machine in the example form of a computer system within which a set of instructions for causing the machine to perform one or more of the methodologies discussed herein may be executed.

FIG. 17 is a block diagram of a computer system that may be used to implement certain features of some of the embodiments of the invention. The computer system may be a server computer, a client computer, a personal computer (PC), a user device, a tablet PC, a laptop computer, a personal digital assistant (PDA), a cellular telephone, an iPhone, an iPad, a Blackberry, a processor, a telephone, a web appliance, a network router, switch or bridge, a console, a hand-held console, a (hand-held) gaming device, a music player, any portable, mobile, hand-held device, wearable device, or any machine capable of executing a set of instructions, sequential or otherwise, that specify actions to be taken by that machine.

The computing system 1000 may include one or more central processing units ("processors") 1002, memory 1004, input/output devices 1008, e.g. keyboard and pointing devices, touch devices, display devices, storage devices, e.g. disk drives, and communications devices 1006, such as network adapters, e.g. network interfaces, that are connected to an interconnect 1010.

In FIG. 17, the interconnect is illustrated as an abstraction that represents any one or more separate physical buses, point-to-point connections, or both connected by appropriate bridges, adapters, or controllers. The interconnect, therefore, may include, for example a system bus, a peripheral component interconnect (PCI) bus or PCI-Express bus, a Hyper-Transport or industry standard architecture (ISA) bus, a small computer system interface (SCSI) bus, a universal serial bus (USB), IIC (12C) bus, or an Institute of Electrical and Electronics Engineers (IEEE) standard 1394 bus, also referred to as Firewire.

The memory and storage devices are computer-readable storage media that may store instructions that implement at least portions of the various embodiments of the invention. In addition, the data structures and message structures may be stored or transmitted via a data transmission medium, e.g. a signal on a communications link. Various communications links may be used, e.g. the Internet, a local area network, a wide area network, or a point-to-point dial-up connection. Thus, computer readable media can include computer-readable storage media, e.g. non-transitory media, and computer-readable transmission media.

The instructions stored in memory can be implemented as software and/or firmware to program one or more processors to carry out the actions described above. In some embodiments of the invention, such software or firmware may be initially provided to the processing system by downloading it from a remote system through the computing system, e.g. via the network adapter.

The various embodiments of the invention introduced herein can be implemented by, for example, programmable circuitry, e.g. one or more microprocessors, programmed with software and/or firmware, entirely in special-purpose hardwired, i.e. non-programmable, circuitry, or in a combination of such forms. Special-purpose hardwired circuitry may be in the form of, for example, one or more ASICs, PLDs, FPGAs, etc.

Although the invention is described herein with reference to the preferred embodiment, one skilled in the art will readily appreciate that other applications may be substituted for those set forth herein without departing from the spirit and scope of the present invention. Accordingly, the invention should only be limited by the Claims included below.

The invention claimed is:

1. A computer implemented method for establishing and maintaining an emergency services management system, comprising:
providing a processor-implemented mobile app in communication with said emergency services management system;
said mobile app performing the steps of:
tracking emergency medical equipment located within a facility comprising a given site, said emergency medical equipment comprising equipment provided for use in pre-hospital, pre-EMS medical emergencies;
tracking said emergency medical equipment operational status,
informing users of said operational status,
receiving maintenance results from said users regarding said emergency medical equipment, and
communicating said maintenance results back to said emergency services management system to confirm on a regular basis that said emergency medical equipment is physically inspected and properly maintained;
said mobile app in communication with a processor-implemented emergency notification application;
said mobile app automatically linking information regarding emergency medical equipment location, maintenance results, and operational status to said emergency notification application;
said emergency notification application receiving said information regarding emergency medical equipment location, maintenance results, and operational status;
said emergency notification application receiving an input signal comprising an initial notification transmitted by a bystander at an emergency within said facility and indicating that there is an emergency;
said emergency notification application receiving said input signal and extracting therefrom content from said bystander comprising identification of a specific location of said emergency and identification of said emergency type;
said emergency notification application automatically selecting laypersons comprising individuals who are regularly present within said facility in a capacity unrelated to emergency medical response and who are trained as responders and said emergency notification application automatically selecting emergency medical equipment within said facility, said selecting of responders and emergency medical equipment based on the type of emergency, the role of the responder, the quality of said responders' training and preparation, actions specified by an organization's emergency response plan, proximity to the emergency, and an operationally/clinically appropriate period of response time;
said emergency notification application automatically selecting both a nearest responder proximate to said emergency medical equipment, and said emergency equipment, based upon known clinical outcomes of a particular emergency type in view of a response time determined by calculating a time equivalent distance between the bystander and the responder and by calculating the time equivalent distance between the bystander and the emergency medical equipment, wherein the distance for the responder to retrieve the emergency medical equipment must be less than a pre-determined maximum time allowed for the response, if the response is to be clinically efficacious, and wherein responders who do not meet the time equivalent distance criteria are not selected; and
during an emergency, said emergency notification application automatically generating a prioritized alert signal for transmission directly to said selected responders, said alert signal comprising said emergency type and said emergency location, and said alert notifying said responders of the location of the nearest operational emergency medical equipment.

2. The method of claim 1, further comprising:
providing a database, maintained by said emergency services management system, containing information for emergency medical equipment for at least one given site, said information comprising serial number, model name, location, expiration date, quantity, and maintenance status.

3. The method of claim 2, further comprising:
said database storing characteristics of one or more of medical equipment, parts, supplies, medications, and non-medical equipment and/or parts and/or supplies.

4. The method of claim 1, further comprising:
associating a provider-supplied, electronically scannable label having associated readable text with said emergency medical equipment in connection with its use at said site.

5. The method of claim 4, further comprising:
a device associated with said mobile app for scanning said label to proceed with maintenance of, or be apprised of any anomalies with, a given piece of emergency medical equipment.

6. The method of claim 4, wherein said label comprises:
provider name;
model;
serial number; and
expiration date.

7. The method of claim 1, further comprising:
providing a master product list for registering one or more complex kits by selection therefrom.

8. The method of claim 1, further comprising:
displaying a list of emergency medical equipment at a site with location and status for each piece of equipment on said list;
providing access to a scanning device when a user selects a piece of emergency medical equipment on said list;
using said scanning device for automatically scanning an electronic label associated with said selected piece of emergency medical equipment;
if said scan is successful, displaying a maintenance checklist and a list of instructions specific to said selected piece of emergency medical equipment; and communicating maintenance results to said emergency services provider.

9. The method of claim 1, further comprising:
registering a user for a maintenance app;
said app communicating with a program management database and verifying that said user is an authorized coordinator for a facility based on said user's first name, last name, email address, and mobile phone number maintained in said program management database;
said app communicating with a server and requesting a list of facility specific emergency medical equipment based on registration data previously entered and verified in said program management database;
said server communicating with said app and requesting a list of facility specific emergency medical equipment from an emergency medical equipment maintenance database;
providing an emergency medical equipment list when said user is an authorized coordinator; and
requesting more information when said user is not an authorized coordinator.

10. The method of claim 9, further comprising:
said user selecting emergency medical equipment from said list;
said app using a scanning device to scan an electronic label on the emergency medical equipment;
said app processing said label and extracting data imbedded therein;
said app comparing said data with the emergency medical equipment selected from the list;
said app populating an inspection checklist based on the emergency medical equipment manufacturer's recommendations for the selected emergency medical equipment make and model when the label data matches the emergency medical equipment data stored in the program management database for the selected emergency medical equipment; and
presenting an error message when the label data does not match the selected emergency medical equipment.

11. The method of claim 10, further comprising:
said app capturing a geo-location of said authorized coordinator when said label is scanned; and
said app reporting said geo-location to said program management database.

12. The method of claim 1, further comprising:
said mobile app and said emergency notification application sharing the same database.

13. The method of claim 1, further comprising:
based on the geo-location of an emergency requiring the use of emergency medical equipment, the geo-location of a facility at which said emergency medical equipment is located, and the operational status recorded for each piece of emergency medical equipment, a program management database determining the location of the emergency medical equipment that is nearest to the location of the emergency, and prioritizing said emergency medical equipment on the basis of operational status.

14. The method of claim 1, further comprising:
said app capturing a geo-location of each piece of emergency medical equipment; and
storing said geo-location in a program management database when the emergency medical equipment is placed into service.

15. The method of claim 1, further comprising:
responsive to said user completing and submitting an emergency medical equipment inspection report, a program management database prioritizing readiness of the emergency medical equipment into categories of: Operational; Alert pending; or Not in service; and
maintaining said information along with the geo-location of the emergency medical equipment.

16. The method of claim 1, further comprising:
said app communicating with a maintenance database; and
sending a notification of a maintenance issue to one or more responsible parties.

17. The method of claim 1, further comprising:
a user's organization pre-authorizing a user to perform an inspection.

18. The method of claim 1, further comprising:
maintaining a local cache of data on a mobile device of an authorized user for authorized emergency medical equipment.

19. The method of claim 1, further comprising:
on a periodic basis, a program management system sending an email notification and/or a text notification to an emergency medical equipment coordinator to complete required emergency medical equipment maintenance.

20. The method of claim 1, further comprising:
said app verifying that an emergency medical equipment coordinator is physically present at the emergency medical equipment location by requiring a responsible party to scan an electronic label that has been placed on or near the emergency medical equipment.

21. The method of claim 1, further comprising:
said app communicating status and requirements with other departments or personnel involved in an organization's emergency medical equipment management program.

22. The method of claim 1, further comprising:
selecting emergency medical equipment based on the type of emergency, the role of the responder, the actions specified by an organization's emergency response plan, and as assessed by a rules engine as to the emergency medical equipment's operational status; and
further selecting said emergency medical equipment based on its proximity to the emergency and a particular emergency responder who has acknowledged that he is responding.

23. The method of claim 1, further comprising:
determining emergency medical equipment operational status by preconfigured rules to ensure that a responder is not directed to equipment that has not been confirmed as being in a specific location, or that has not been recently inspected, or that has expired accessories, or that has been determined to have an issue pending resolution.

24. The method of claim 1, further comprising:
tracking the return of non-operational equipment to operational status.

25. An apparatus for establishing and maintaining an emergency services management system, comprising:
a mobile app in communications with an emergency services management system;
said mobile app performing the processor-implemented steps of:
tracking emergency medical equipment located within a facility comprising a given site, said emergency medical equipment comprising equipment provided for use in pre-hospital, pre-EMS medical emergencies;

tracking said emergency medical equipment status, informing users of said status, receiving maintenance results from said users regarding said emergency medical equipment, and communicating said maintenance results back to said emergency services provider to confirm on a regular basis that said emergency medical equipment is physically inspected and properly maintained;

said mobile app in communication with a processor-implemented emergency notification application;

said mobile app further performing the processor-implemented step of automatically linking information regarding emergency medical equipment location, maintenance results, and operational status to said processor-implemented emergency notification application;

said emergency notification application receiving said information regarding emergency medical equipment location, maintenance results, and operational status;

said emergency notification application receiving an input signal comprising an initial notification transmitted by a bystander at an emergency within said facility and indicating that there is an emergency;

said emergency notification application receiving said input signal and extracting therefrom content from said bystander comprising identification of a specific location of said emergency and identification of said emergency type;

said emergency notification application automatically selecting laypersons comprising individuals who are regularly present within said facility in a capacity unrelated to emergency medical response and who are trained as responders and said emergency notification application automatically selecting emergency medical equipment within said facility, said selecting of responders and emergency medical equipment based on the type of emergency, the role of the responder, the quality of said responders' training and preparation, actions specified by an organization's emergency response plan, proximity to the emergency, and an operationally/clinically appropriate period of response time;

said emergency notification application automatically selecting both a nearest responder proximate to said emergency medical equipment, and said emergency equipment, based upon known clinical outcomes of a particular emergency type in view of a response time determined by calculating a time equivalent distance between the bystander and the responder and by calculating the time equivalent distance between the bystander and the emergency medical equipment, wherein the distance for the responder to retrieve the emergency medical equipment must be less than a pre-determined maximum time allowed for the response, if the response is to be clinically efficacious, and wherein responders who do not meet the time equivalent distance criteria are not selected; and during an emergency, said emergency notification application automatically generating a prioritized alert signal for transmission directly to said selected responders, said alert signal comprising said emergency type and said emergency location, and said alert notifying said responders of the location of the nearest operational emergency medical equipment.

* * * * *